US008556954B2

(12) United States Patent
Ben Muvhar et al.

(10) Patent No.: US 8,556,954 B2
(45) Date of Patent: Oct. 15, 2013

(54) METHODS FOR TREATING ABNORMAL GROWTHS IN THE BODY USING A FLOW REDUCING IMPLANT

(75) Inventors: Shmuel Ben Muvhar, Tirat Zvi (IL); Ilan Shalev, Givataim (IL); Jonathan Tsehori, Ramat Gan (IL); Nissim Darvish, Tzrufa (IL)

(73) Assignee: Neovasc Medical Ltd (IL)

( * ) Notice: Subject to any disclaimer, the term of this patent is extended or adjusted under 35 U.S.C. 154(b) by 135 days.

(21) Appl. No.: 12/603,518

(22) Filed: Oct. 21, 2009

(65) Prior Publication Data

US 2010/0114299 A1    May 6, 2010

Related U.S. Application Data

(63) Continuation of application No. 10/491,976, filed as application No. PCT/IL02/00805 on Oct. 3, 2002, now abandoned, which is a continuation-in-part of application No. 09/534,968, filed on Mar. 27, 2000, now Pat. No. 6,953,476, and a continuation-in-part of application No. PCT/IL01/00284, filed on Mar. 27, 2001.

(30) Foreign Application Priority Data

Oct. 4, 2001  (IL) .......................................... 145750
Aug. 8, 2002  (IL) .......................................... 151162

(51) Int. Cl.
  *A61F 2/06*  (2013.01)
(52) U.S. Cl.
  USPC ....................................................... 623/1.11

(58) Field of Classification Search
  None
  See application file for complete search history.

(56) References Cited

U.S. PATENT DOCUMENTS

| | | | |
|---|---|---|---|
| 3,334,629 A | 8/1967 | Cohn | |
| 3,620,218 A | 11/1971 | Schmitt | |
| 4,106,129 A | 8/1978 | Carpentier et al. | |
| 4,292,974 A | 10/1981 | Fogarty et al. | |
| 4,297,749 A | 11/1981 | Davis et al. | |
| 4,494,531 A | 1/1985 | Gianturco | |

(Continued)

FOREIGN PATENT DOCUMENTS

| DE | 2613575 A1 | 9/1977 |
|---|---|---|
| DE | 3918736 A1 | 12/1990 |

(Continued)

OTHER PUBLICATIONS

Beck, et al. Operations for coronary artery disease. J Am Med Assoc. Nov. 27, 1954;156(13):1226-33.

(Continued)

*Primary Examiner* — Melanie Tyson
(74) *Attorney, Agent, or Firm* — Wilson, Sonsini, Goodrich & Rosati

(57) ABSTRACT

Methods of using flow reducing implants for treatment of abnormal growths in the body are described. In embodiments of the claimed subject matter, a source blood vessel feeding the abnormal growth is first determined, and a flow reducing implant is then inserted into the source blood vessel to reduce the blood flow through the source blood vessel. The flow reducing implant includes at least one flared section for contacting a blood vessel wall, and at least one narrowed section defining a flow passage. Anchor tabs that lie generally in a plane of the flared section may also be employed.

11 Claims, 23 Drawing Sheets

(56) References Cited

U.S. PATENT DOCUMENTS

| | | |
|---|---|---|
| 4,501,263 A | 2/1985 | Harbuck |
| 4,601,718 A | 7/1986 | Possis et al. |
| 4,705,517 A | 11/1987 | DiPisa, Jr. |
| 4,727,873 A | 3/1988 | Mobin |
| 4,776,337 A | 10/1988 | Palmaz |
| 4,787,388 A | 11/1988 | Hofmann |
| 4,813,934 A | 3/1989 | Engelson et al. |
| 4,893,623 A | 1/1990 | Rosenbluth |
| 4,994,066 A | 2/1991 | Voss |
| 5,007,926 A | 4/1991 | Derbyshire |
| 5,026,377 A | 6/1991 | Burton et al. |
| 5,064,435 A | 11/1991 | Porter |
| 5,078,736 A | 1/1992 | Behl |
| 5,129,902 A | 7/1992 | Goble et al. |
| 5,201,757 A | 4/1993 | Heyn et al. |
| 5,209,727 A | 5/1993 | Radisch, Jr. et al. |
| 5,211,654 A | 5/1993 | Kaltenbach |
| 5,222,980 A | 6/1993 | Gealow |
| 5,246,445 A | 9/1993 | Yachia et al. |
| 5,282,823 A | 2/1994 | Schwartz et al. |
| 5,304,194 A | 4/1994 | Chee et al. |
| 5,304,220 A | 4/1994 | Maginot |
| 5,330,482 A | 7/1994 | Gibbs et al. |
| 5,342,348 A | 8/1994 | Kaplan |
| 5,354,309 A | 10/1994 | Scinepp-Pesch et al. |
| 5,375,612 A | 12/1994 | Cottenceau et al. |
| 5,382,261 A | 1/1995 | Palmaz |
| 5,397,351 A | 3/1995 | Pavcnik et al. |
| 5,397,355 A | 3/1995 | Marin et al. |
| 5,409,019 A | 4/1995 | Wilk |
| 5,425,765 A | 6/1995 | Tiefenbrun et al. |
| 5,464,449 A | 11/1995 | Ryan et al. |
| 5,476,506 A | 12/1995 | Lunn |
| 5,500,014 A | 3/1996 | Quijano et al. |
| 5,514,176 A | 5/1996 | Bosley |
| 5,554,152 A | 9/1996 | Aita et al. |
| 5,554,185 A | 9/1996 | Block et al. |
| 5,575,818 A | 11/1996 | Pinchuk |
| 5,609,574 A | 3/1997 | Kaplan et al. |
| 5,609,627 A | 3/1997 | Goicoechea et al. |
| 5,618,301 A | 4/1997 | Hauenstein et al. |
| 5,620,439 A | 4/1997 | Abela et al. |
| 5,645,551 A | 7/1997 | Green et al. |
| 5,653,743 A | 8/1997 | Martin |
| 5,653,744 A | 8/1997 | Khouri |
| 5,655,548 A | 8/1997 | Nelson et al. |
| 5,662,713 A | 9/1997 | Andersen et al. |
| 5,683,411 A | 11/1997 | Kavteladze et al. |
| 5,695,504 A | 12/1997 | Giford, III et al. |
| 5,709,335 A | 1/1998 | Heck |
| 5,713,908 A | 2/1998 | Jameel et al. |
| 5,716,393 A | 2/1998 | Lindemberg et al. |
| 5,732,872 A | 3/1998 | Bolduc et al. |
| 5,741,333 A | 4/1998 | Frid |
| 5,755,769 A | 5/1998 | Richard et al. |
| 5,755,779 A | 5/1998 | Horiguchi |
| 5,772,668 A | 6/1998 | Summers et al. |
| 5,776,164 A | 7/1998 | Ripart |
| 5,782,844 A | 7/1998 | Yoon et al. |
| 5,782,905 A | 7/1998 | Richter |
| 5,797,930 A | 8/1998 | Ovil |
| 5,797,935 A | 8/1998 | Barath |
| 5,810,850 A | 9/1998 | Hathaway et al. |
| 5,840,081 A | 11/1998 | Andersen et al. |
| 5,843,117 A | 12/1998 | Alt et al. |
| 5,863,284 A | 1/1999 | Klein |
| 5,873,906 A | 2/1999 | Lau et al. |
| 5,876,418 A | 3/1999 | Karlheinzhauen-Stein et al. |
| 5,876,445 A | 3/1999 | Andersen et al. |
| 5,897,588 A | 4/1999 | Hull et al. |
| 5,919,224 A | 7/1999 | Thompson et al. |
| 5,925,063 A | 7/1999 | Khosravi |
| 6,013,055 A | 1/2000 | Bampos et al. |
| 6,015,432 A | 1/2000 | Rakos et al. |
| 6,053,873 A | 4/2000 | Govari et al. |
| 6,070,589 A | 6/2000 | Keith et al. |
| 6,071,292 A | 6/2000 | Makower et al. |
| 6,110,198 A | 8/2000 | Fogarty et al. |
| 6,120,534 A | 9/2000 | Ruiz |
| 6,129,706 A | 10/2000 | Janacek |
| 6,159,156 A | 12/2000 | Van Bockel |
| 6,165,211 A | 12/2000 | Thompson |
| 6,168,614 B1 | 1/2001 | Andersen et al. |
| 6,254,601 B1 | 7/2001 | Burbank et al. |
| 6,254,627 B1 | 7/2001 | Freidberg |
| 6,277,082 B1 | 8/2001 | Gambale |
| 6,293,968 B1 | 9/2001 | Taheri |
| 6,296,603 B1 | 10/2001 | Tumlund et al. |
| 6,325,813 B1 | 12/2001 | Hektner et al. |
| 6,348,066 B1 | 2/2002 | Pinchuk et al. |
| 6,447,539 B1 | 9/2002 | Nelson et al. |
| 6,579,306 B1 | 6/2003 | Voelker et al. |
| 6,579,314 B1 | 6/2003 | Lombardi et al. |
| 6,638,293 B1 * | 10/2003 | Makower et al. .............. 606/200 |
| 6,641,610 B2 | 11/2003 | Wolf et al. |
| 6,953,476 B1 | 10/2005 | Shalev |
| 2001/0021872 A1 | 9/2001 | Bailey et al. |
| 2002/0042646 A1 | 4/2002 | Wall |
| 2002/0151924 A1 | 10/2002 | Shiber |
| 2003/0163148 A1 | 8/2003 | Wang et al. |
| 2004/0158280 A1 | 8/2004 | Morris et al. |
| 2005/0055082 A1 | 3/2005 | Ben Muvhar |
| 2005/0267567 A1 | 12/2005 | Shalev |
| 2006/0106449 A1 | 5/2006 | Ben Muvhar |
| 2006/0106450 A1 | 5/2006 | Ben Muvhar |
| 2010/0114299 A1 | 5/2010 | Ben Muvhar et al. |

FOREIGN PATENT DOCUMENTS

| | | |
|---|---|---|
| DE | 9101344 U1 | 8/1991 |
| DE | 19509464 C1 | 6/1996 |
| EP | 0117940 B1 | 9/1984 |
| EP | 0355341 A1 | 2/1990 |
| EP | 0441516 B1 | 8/1991 |
| EP | 0461791 A1 | 12/1991 |
| EP | 0556850 A1 | 8/1993 |
| EP | 0587197 A1 | 3/1994 |
| EP | 0621015 A1 | 10/1994 |
| EP | 0696446 A1 | 2/1996 |
| EP | 0779062 A1 | 6/1997 |
| FR | 2688688 A1 | 9/1993 |
| FR | 2743293 A1 | 7/1997 |
| JP | 07-112028 A | 5/1995 |
| JP | 11-501526 A | 2/1999 |
| WO | WO 92/06734 A1 | 4/1992 |
| WO | WO 93/08767 A1 | 5/1993 |
| WO | WO 93/22986 A1 | 11/1993 |
| WO | WO 94/24961 A1 | 11/1994 |
| WO | WO 95/08965 A1 | 4/1995 |
| WO | WO 95/21592 A1 | 8/1995 |
| WO | WO 95/26695 A1 | 10/1995 |
| WO | WO 95/31155 A1 | 11/1995 |
| WO | WO 97/27898 A1 | 8/1997 |
| WO | WO 98/46115 A2 | 10/1998 |
| WO | WO 99/34731 A1 | 7/1999 |
| WO | WO 99/65418 A1 | 12/1999 |
| WO | WO 00/32092 A1 | 6/2000 |
| WO | WO 01/72239 A2 | 10/2001 |
| WO | WO 2004/014257 A1 | 2/2004 |
| WO | WO 2004/014474 A1 | 2/2004 |

OTHER PUBLICATIONS

Beck, et al. Scientific basis for the surgical treatment of coronary artery disease. J Am Med Assoc. Nov. 26, 1955;159(13):1264-71.

Beck, et al. Some new concepts of coronary heart disease; results after surgical operation. J Am Med Assoc. Dec. 20, 1958;168(16):2110-7.

Beck, et al. The coronary patient wants better treatment. Med Times. Jan. 1961;89:17-26.

Beck, et al. The surgical management of coronary artery disease: background, rationale, clinical experiences. Ann Intern Med. Dec. 1956;45(6):975-88.

(56) References Cited

OTHER PUBLICATIONS

Braunwald. Heart Disease: A textbook of Cardiovascular Medicine. 5th Edition; W. B. Saunders Company. 1997; Chapter 36; pp. 1168-1169.

Brofman. Long term influence of the Beck operation for coronary heart disease. Am J Cardiol. Aug. 1960;6:259-71.

European search report dated Jan. 25, 2007 for EP Application No. 02772791.6.

Faxon, et al. Coronary sinus occlusion pressure and its relation to intracardiac pressure. Am J Cardiol. Sep. 1, 1985;56(7):457-60.

Gross, et al. Experimental attempts to increase the blood supply to the dog's heart by means of coronary sinus occlusion. J. Exper. Med. Jan. 1937; 65:91-108 and plates 4-5.

Office action dated Mar. 26, 2008 for U.S. Appl. No. 10/523,966.

Office action dated Apr. 21, 2009 for U.S. Appl. No. 10/491,976.

Office action dated May 18, 2007 for U.S. Appl. No. 10/523,966.

Office action dated Aug. 28, 2008 for U.S. Appl. No. 10/491,976.

Office action dated Dec. 24, 2008 for U.S. Appl. No. 10/523,966.

Robertson. The reestablishment of cardiac circulation during progressive coronary occlusion. The American Heart Journal. 1935; 10:533-541.

Sandler, et al. The Beck operation in the treatment of angina pectoris. Thorax. Jan. 1967;22(1):34-7.

Wising. The Beck-I operation for angina pectoris: medical aspects. Acta Med Scand. Jul. 1963;174:93-8.

Zalewski, et al. Myocardial protection via coronary sinus interventions: superior effects of arterialization compared with intermittent occlusion. Circulation. Jun. 1985; 71(6):1215-1222.

\* cited by examiner

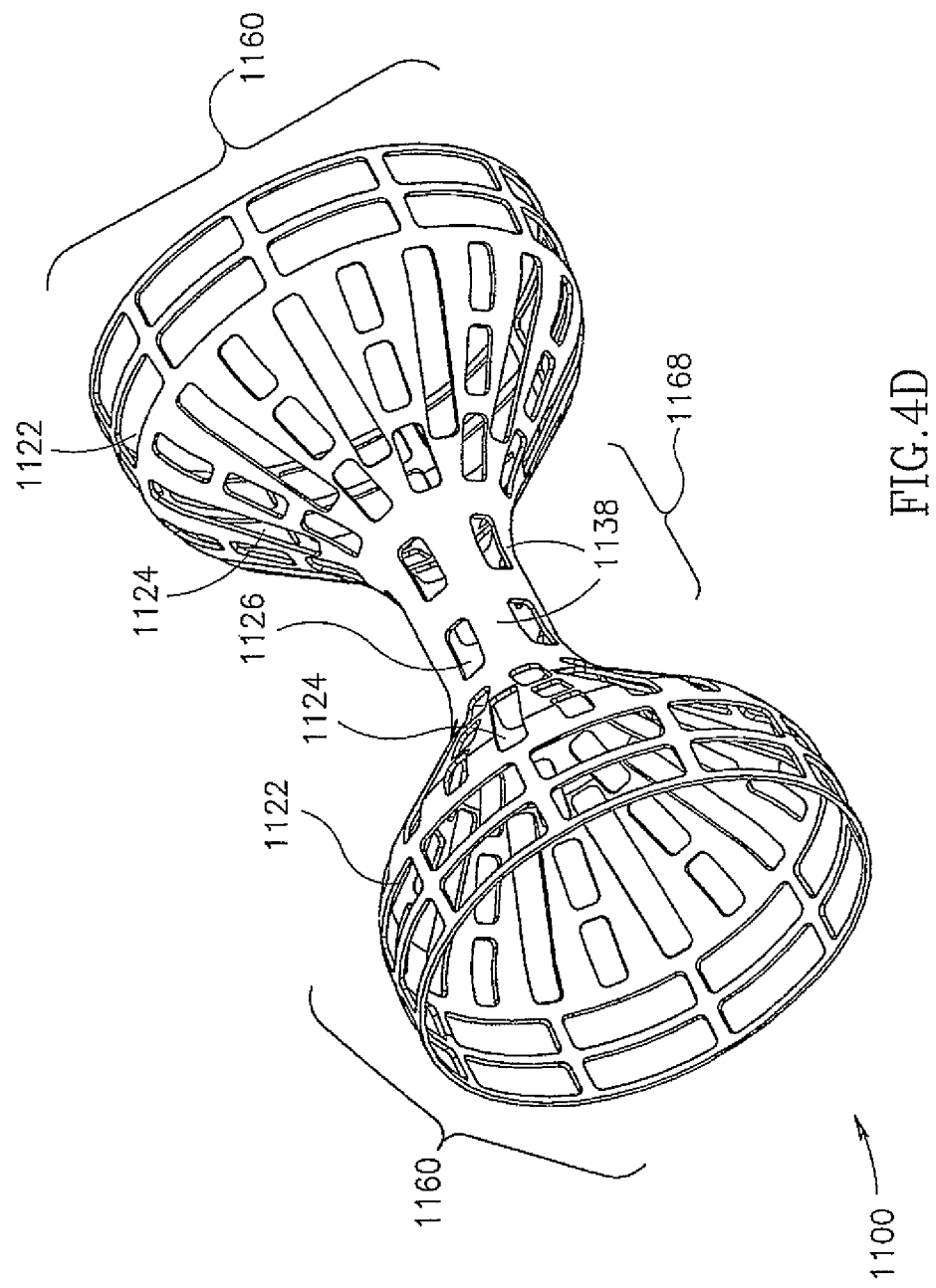

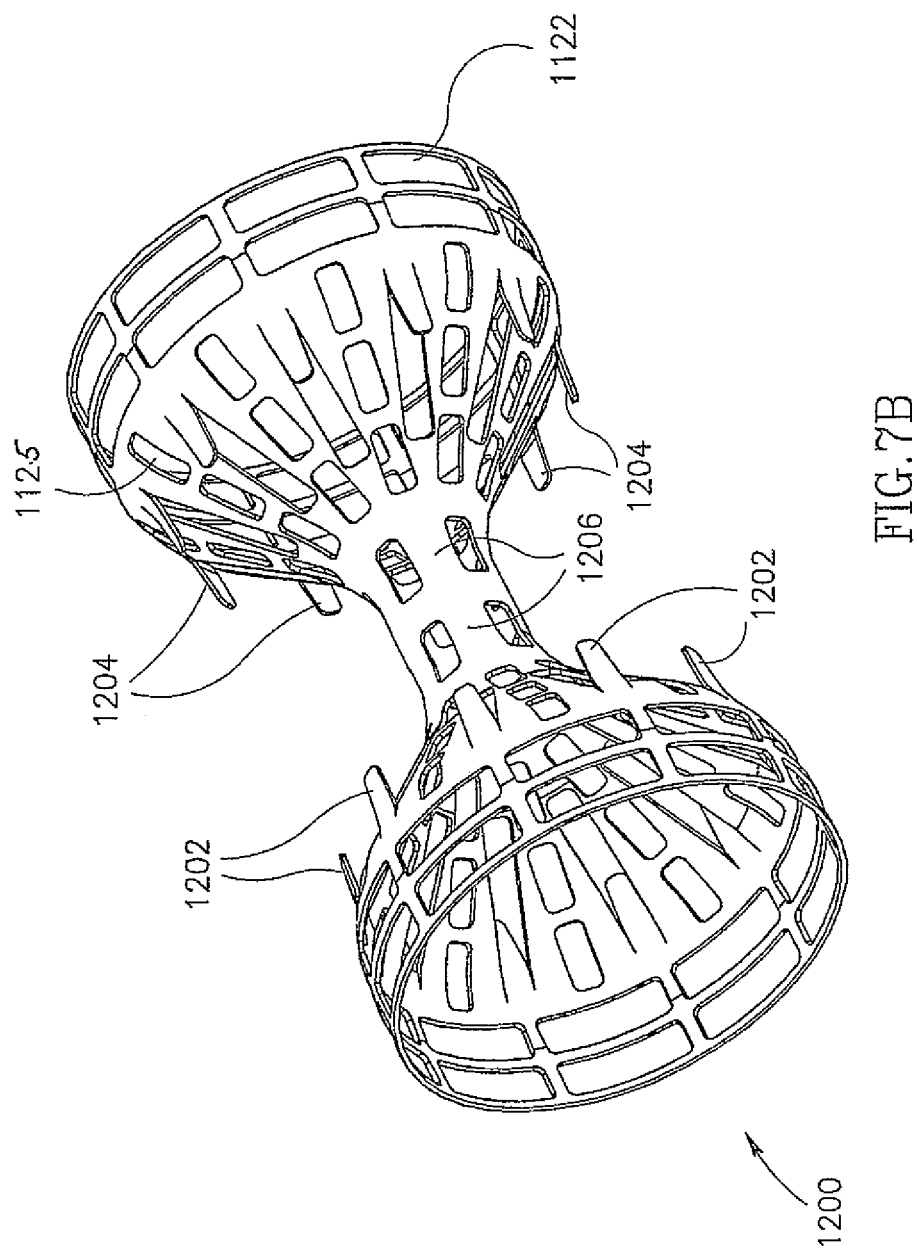

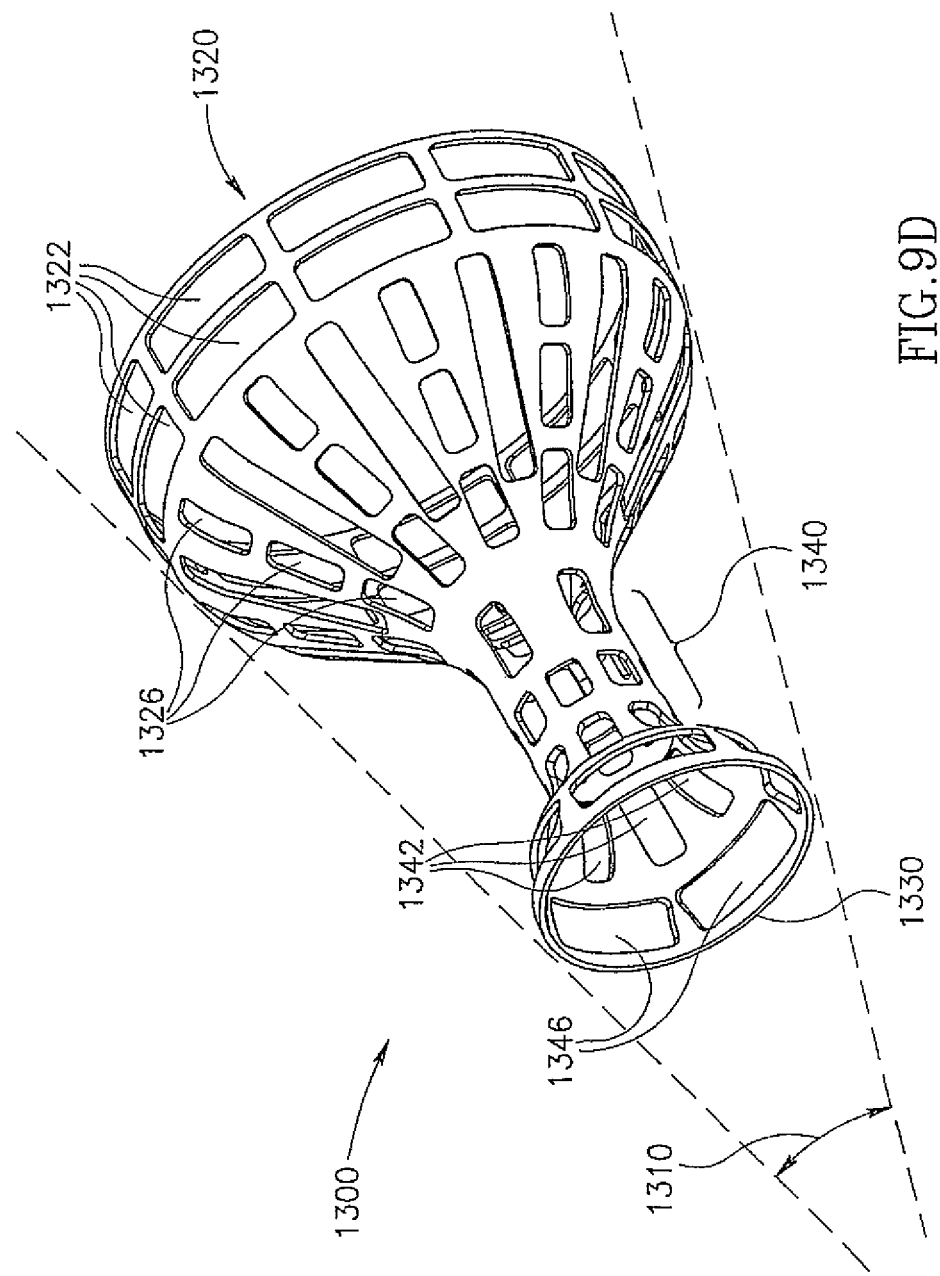

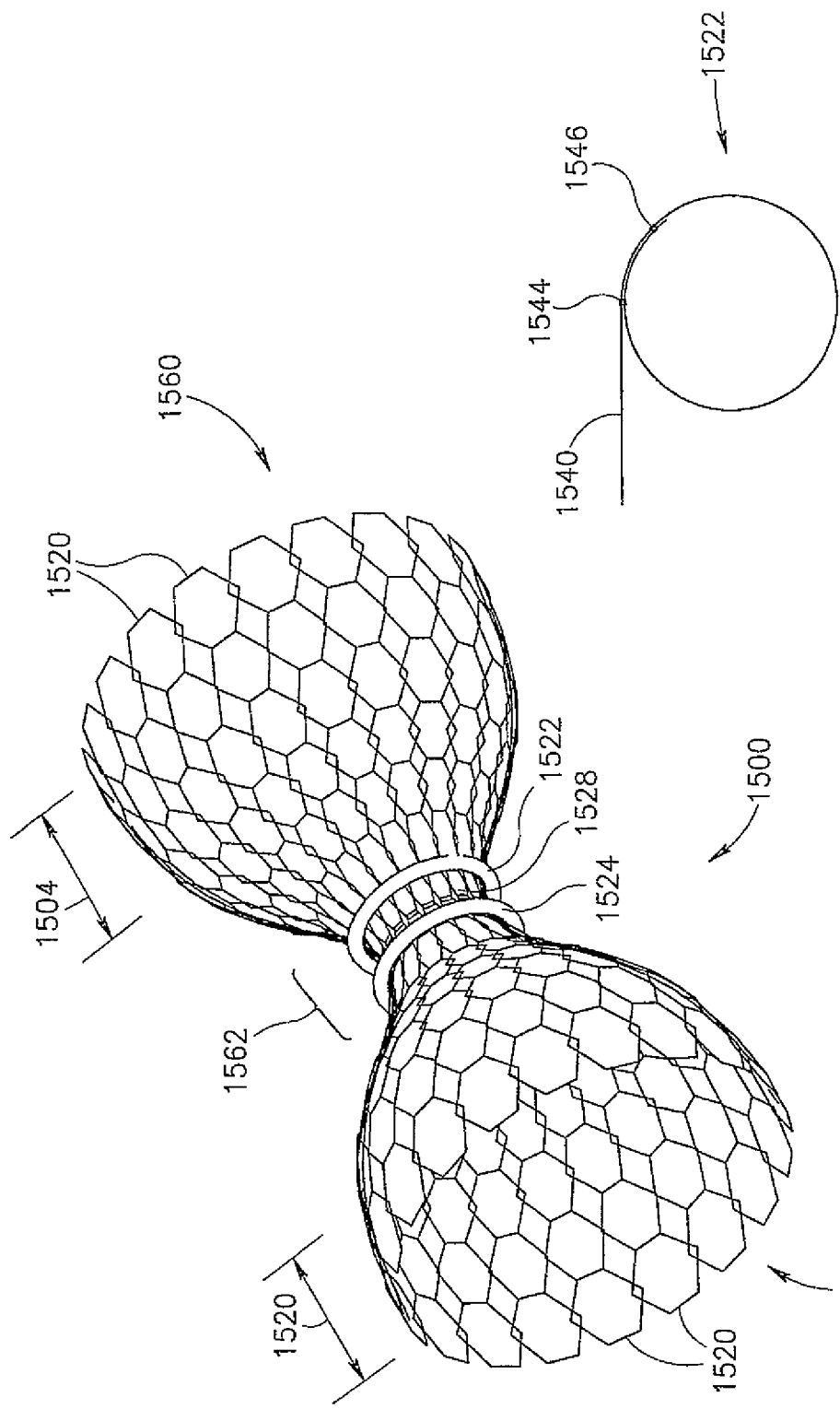

METHODS FOR TREATING ABNORMAL GROWTHS IN THE BODY USING A FLOW REDUCING IMPLANT

RELATED APPLICATIONS

This application is a continuation of U.S. application Ser. No. 10/491,976 filed on Oct. 8, 2004 (now abandoned), filed as PCT application No. PCT/IL2002/000805 on Oct. 3, 2002, which designates the U.S. and which published in English, which is a continuation-in-part of PCT application No. PCT/IL2001/000284 filed on Mar. 27, 2001, which designates the U.S. and which published in English, which is a continuation-in-part of U.S. application Ser. No. 09/534,968 filed Mar. 27, 2000, the technical disclosure of all of which are incorporated herein by reference. This application also claims the priority of Israel application Nos. 145750 filed Oct. 4, 2001 and 151162 filed Aug. 8, 2002, the technical disclosure of all of which are incorporated herein by reference.

FIELD OF THE INVENTION

The present invention relates to implants for reducing flow through bodily conduits, for example, blood vessels.

BACKGROUND OF TAE INVENTION

The heart pumps blood through the body. The heart itself is fed by coronary arteries that end at capillaries. The capillaries are drained by a network of coronary veins, that (typically) flow into a vein known as the coronary sinus. The coronary sinus is a short, large diameter vein that is substantially contiguous with a right atrium, the atrium that collects all venous blood from the body.

Occlusion of coronary arteries is a leading cause of death, especially sudden death, in what is commonly called a "heart attack". When blood flow to a portion of the heart is suddenly stopped, the portion becomes ischemic and its electrical activity is disrupted. As the activity of the heart is mediated by electrical signal propagation, such disruption typically propagates to the rest of the heart, disorganizes the heart's activation and causes the heart output to be reduced drastically, which leads to ischemia and death of the brain. In addition, the disorganized activity often damages the heart beyond what was caused directly by the blockage.

If a patient survives the direct effects of the heart attack, the damage to the heart may predispose the patient to future electrical disorders and/or may significantly reduce the cardiac output, thus reducing quality of life and life expectancy.

Angina pectoris is a chronic or semi-chronic condition that, while not life-threatening, significantly reduces quality of life. In general, the heart responds to increased demand by working harder, requiring more coronary blood flow. When coronary arteries are stenosed or occluded, the increased blood flow cannot be provided, and pain, caused by the resulting ischemia, is produced.

The heart has natural mechanisms to overcome stenosis in coronary arteries. One such mechanism is angiogenesis, in which new arteries are created, for bypassing the stenosis.

Since angiogenesis sometimes does not occur naturally, various procedures have been suggested to encourage it. For example Trans-Myocardial Revascularization (TMR), is a process in which multiple holes are drilled in the heart, with the intent of causing new vessels to be created.

Beck, in "The Surgical Management of Coronary Artery Disease: Background, Rationale, Clinical Experience" by C. S. Beck and B. L. Brofman, 1956, by the American College of Physicians in Annals of Internal Medicine Vol. 45, No. 6, December 1956 and in "Long Term Influence of the Beck Operation for Coronary Heart Disease", by B. L. Brofman in the American Journal of Cardiology August 1960, the disclosures of which are incorporated herein by reference, performed open chest surgery in which a coronary sinus vein was restricted, by an external suture. After a few months, coronary blood supply apparently improved. However, this method has fallen in disfavor, in part possibly due to the need to open the chest and lift up the heart, to reach the coronary sinus vein.

A standard treatment of stenosed arteries is inserting a stent into the artery, at the stenosed point. The stent, for example a metal coil or mesh, is expanded to have an inner diameter similar to that of the original stenosed blood vessel. If many and/or elongated stenoses are present, it is not common to implant multiple stents. Instead, a bypass procedure, in which a conduit is used to bypass the stenoses, is performed.

U.S. Pat. No. 5,618,301, the disclosure of which is incorporated herein by reference, describes a stent-like device for reducing the diameter of a body conduit. What is described is an open mesh stent that can be inserted in a channel created by a TIPS (Trans-Jugular Intra-Hepatic Portal-Systemic Shunt) procedure, to reduce the blood flow rate through the channel, In order to ensure the flow diameter is reduced and prevent flow through the open mesh, a plurality of thrombogentic threads are provided on the outside of the mesh. However, as can be appreciated, intentionally forming thrombosis in most any part of the vascular system, and especially near the heart, can lead to propagating coagulation or floating thromboses, which are potentially fatal.

SUMMARY OF THE INVENTION

An aspect of some embodiments of the invention relates to an anchor for a flow reducing implants adapted for insertion into a blood vessel. In an exemplary embodiment of the invention, one or more tabs are provided on a circumference of the reducing implant. In an exemplary embodiment of the invention, these tabs engage the blood vessel wall if the implant moves axially relative to the blood vessel and are, for example, extended axially towards or away from the reducing implant. Alternatively or additionally, these tabs prevent rotational motion. In some embodiments of the invention, the tabs are not exactly aligned with the axis of the blood vessel, for example, being pointed towards the wall of the blood vessel or being angled relative to the axis, but in the plane of the blood vessel wall. In an exemplary embodiment of the invention, the tabs are elastically pre-stressed to extend in the desired direction. Alternatively, the tabs are formed out of a same sheet material as the reducing implant. and the implant is of a type where one portion is narrowed and another is flared. The tabs are attached to the flared portion and cut away from the narrowed portion, so that when the reducing implant is deployed the tabs continue in a same plane as the flared portion.

Optionally, the tabs dig into the blood vessel wall and/or are adapted to encourage tissue ingrowth or other biological or physical anchoring effects.

An aspect of some embodiments of the invention relates to varying slit geometry in a reducing implant to effect a control over the expanded shape of the reducer. In an exemplary embodiment, a slit-type flow reducing implant comprises a matrix, for example a sheet of metal into which one or more slits are cut. The one or more slits serve to govern the contour of an expanded configuration of the slit-type flow reducing implant. In an exemplary embodiment, the slit-type reducing implant is delivered to the implantation site in a contracted size, for example within a delivery sheath, and expanded to is final configuration at the deployment site. Said expansion, for example, employs the use of a balloon expansion catheter, for example, that exerts appropriate expansion force on the walls of the lumen of the flow reducing implant so that the slits expand and the implant attains its final configuration.

In an exemplary embodiment of the invention, the one or more narrowed sections are non-expandable, expand less and/or require a greater force to cause them to expand, as compared to flared sections. In this manner, using expansion force provided by a standard balloon catheter that expands within the lumen of the flow reducing implant, the implant achieves its final configuration comprising at least one flared section and at least one narrowed section.

Alternatively or additionally, at least a portion the flow reducing implant is self expanding (e.g., shape-memory, elastic or super elastic). Optionally, the flow reducing implant comprises materials with a shape memory so the flow reducing implant automatically attains a desired shape following release, for example, from a delivery catheter into the coronary sinus.

In an exemplary embodiment of the invention, the flow reducing implant comprises a rim, for example along the flared edge, that is constructed to be more difficult to expand (for plastic) or expand less (for self-expanding) than portions of the flow reducing implant just inside the rim.

In an exemplary embodiment, the slits of the slit-type reducing implant can be varied in width, thickness (of surrounding material) density, length and/or orientation thereby providing specific expanded configurations to the implant (e.g., self-expanding or actively expanded). In this manner, flow reducing implants providing different configurations, for example, filling the flow reduction needs of a variety of environments in the body, can be provided. Alternatively or additionally, the variations may affect the order in which parts expand and/or the response to an external pressure, thus possibly allowing various effects to be achieved from a single reducing implant. Alternatively or additionally, the variations may affect the amount of blood flow through the reducer walls.

For example, one or more slits may be provided in the flared section of the flow reducing implant walls that are oriented transverse, oblique and/or longitudinal to the flow reducing implant flow passage. As a result, the flared section expands to a specific contour, for example, with a gradual slope, to fit a specific blood vessel and/or provide a spatial blood flow profile. Optionally, the slits governing the configuration of the flow reducing implant are arranged so that the implant achieves a configuration that is asymmetric.

In an exemplary embodiment, a flow reducing implant comprises a smooth edge along its rim, defined, for example by the pattern of slits. The smooth edge, for example, reduces irritation to the tissue, for example to venous tissue that is often more delicate than arterial walls.

In an exemplary embodiment, a mesh-type flow reducing implant comprises a woven open material, for example of metal and/or plastic fibers, using methods well known in the art.

In an exemplary embodiment, a mesh-type or woven flow reducing implant comprises a covering that restricts blood flow through the wall of the narrow area of the flow reducing implant while one or more portions of the flared sections are not covered. Optionally, at least one portion of one or more of the uncovered flared section is adapted to interface with the blood vessel wall, for example anchoring the implant in the blood vessel wall. Optionally, the flow reducing implant is coated with a flexible coating (inside and/or out) and/or defines a densely woven mesh pattern and/or slit pattern, that prevents or reduces blood flow through the flow reducing implant surface, for example, forcing at least 40%, 60%, 80%, 90% or any smaller, greater or intermediate flow percentage to be through an axial lumen defined by said flow reducing implant. In an exemplary embodiment of the invention, the dense mesh and/or dense slits fill at least 30%, 40%, 60%, 70%, 80% or any greater, smaller or intermediate percentage of a surface of the flow reducing implant.

Some features described for a woven mesh-type reducing implant may be applied to a slit-type reducing implant and embodiments described for a slit-type reducing implant may be applied to a mesh-type reducing implant. In addition, an aspect of some embodiments includes structural improvement that are less specific to the type of implant material.

In an exemplary embodiment of the invention, the reducer is formed of a thick material, possibly with a constant outer diameter, with the flared out portions being formed by thinning the inside layer of the reducer. The reducer may be, for example expanding or it may be simply crimped, so that it expands uniformly along its length, like a stmt. Alternatively or additionally, this structure is used to assist in differentiating the inner diameters of different parts of an expanding reducer.

An aspect of some embodiments of the invention relates to a flow reducing implant that may be modified following implantation in a blood vessel, for example a coronary sinus and/or artery. For example, such modifications may be made in the size of its flared and/or narrowed sections, shape or configuration and/or in situ location.

In an exemplary embodiment of the invention, the blood flow exiting a flow reducing implant is modified by inserting an insert into the narrow and/or flared sections of the flow reducing implant. In an exemplary embodiment of the invention, the inserted body comprises a funnel with a variable diameter, such diameter being determined by the diameter of surrounding implant. For example, as the in variable insert is pressed into a flared section with a gradual slope, the size of the funnel insert and/or hole at its apex, is reduced, thereby reducing the blood flow through the flow reducing implant.

Alternatively or additionally, the flow reducing implant includes a set of apertures on its narrow section and/or a set of hooks or other engagable elements adapted to be engaged by a catheter that is inserted into the reducer. The catheter engages the flow reducing implant and pulls in radially on the walls, for example, of the narrowed section, to reduce its diameter.

Alternatively or additionally, one or more rings or cords, is provided around some or all of the circumference of the narrowing (or other part of the reducer implant). These rings may prevent expansion. Alternatively or additionally, when sufficient pressure is applied, the rings (or cord) may tear and greater expansion (e.g., to the limits defined by the device or a next ring, under the applied pressure, are achieved). Alternatively or additionally, the ring is elastic and when sufficient pressure is applied, the implant expands plastically, until the point where the applied pressure is smaller than the sum of the resistance of the implant and the resistance of the ring. Once the pressure is removed, the force applied by the ring is not enough to collapse the implant, for example, due to the rigidity of the implant or due to the change in geometry of the implant.

Alternatively or additionally to providing multiple rings, each with a different breaking point, a belt with multiple stop points may be provided. For example, each time pressure is increased, the belt may jump one stop, thereby allowing some expansion of the narrowing. The stop points may, for example, offer equal or increasing resistance to jumping.

Optionally, when a cord is provided, it is weaved into the reducer implant, possibly serving to block flow through the implant wall additionally or alternatively to determining its geometry. Optionally, the length of cord can be varied by a physician, for example before implantation, or after, for example by engaging the cord and pulling it to reduce the reducing implant narrow diameter.

In some embodiments of the invention, the flow reducing implant wall at the narrowing is formed by overlapping scales (e.g., by "U" shaped cuts cut out of the implant wall). As the cord expands, the edges on the at least one wall of the cord-type flow reducing implant move in relation to each other, thereby providing one or more expansion diameters. In an exemplary embodiment of the invention, the original diameter of the narrowed section of the implant is greater than that of the deployed device. Providing such "U" shaped cuts (e.g., with the tongue of the "U" pointing perpendicular to the axis), allows the narrowed section to be compressed, whereby the "U" tongues overlap like scales, inside the lumen of the implant and/or outside of the lumen.

Alternatively or additionally, the implant may be formed of a rolled sheet material, with overlap. As the implant is expanded, the overlap between parts of the sheet is reduced. Optionally, the initial overlap is set by a cord.

In an exemplary embodiment, a plurality of rings are provided and are spaced axially apart from each other, limiting the expansion of the section between them. A plurality of such rings may also be used to define the expanded geometry to be other than a simple, symmetric narrowing. For example to define the slope of the narrowing.

In an exemplary embodiment of the invention, the ring is an inflatable balloon, for example mounted on the outside of the reducing implant or formed by the surfaces of the implant. In an exemplary embodiment of the invention, as the balloon is inflated more, the reducing implant inner diameter lessens. In an exemplary embodiment of the invention, the balloon is inflated outside the body. Alternatively or additionally, it is inflated during implantation. Alternatively or additionally, the balloon is inflated after the fact, for example by guiding a needle catheter to the implant, piecing the balloon with the needle and injecting a fluid through the needle. Optionally, the balloon is backed by a tough layer, for example kevlar to prevent over penetration of the needle. Alternatively or additionally, the needle catheter is shaped to match the narrowing geometry and thus ensure correct placement. Alternatively or additionally, the needle length is limited by a stop so it cannot penetrate far past the reducer implant wall.

Alternatively or additionally, to an inflated balloon, the balloon may be self inflating, for example being formed of (or filled with) a material that expands under moist conditions.

In an exemplary embodiment of the invention, the reducer is surrounded by an active band, for example including a motor which is activated by external signals (e.g., RF ultrasound or magnetic fields) to shorten or lengthen the effective length of the band.

Alternatively or additionally to providing a mechanism for changing a narrowing, other flow control methods may be used. In one example, one or more flaps or ribbons selectively extend into the lumen of the reducing implant. Such ribbons or flaps may be selectively torn and/or bent flat to the vessel wall, for example during or after deployment. Alternatively or additionally, the reducing implant may include two coaxial reducing implants, with slots that can be selectively aligned. If the slots are misalign, flow through the walls of the reducing implants is reduced. If the slots are aligned, such flow is increased. The reducing implants may be selected to be alignable over their entire length. Alternatively, for example if an hour-glass shaped reducing implant is used, one flared section may be designed to be mis-aligned when the other flared section is aligned. Optionally, this embodiment is used to select if blood should flow into or out of the space between the implant and the blood wall, possibly affecting collapse of the vessel wall on the implant. The two reducing implants are, in some embodiments of the invention aligned inside the body. Alternatively or additionally, they are aligned outside the body. Optionally, the inner reducing implant is adapted to be mounted inside a reducing implant, rather than a vessel wall, for example, including short hard radial anchors, rather than a soft, smooth coating on its edge.

An aspect of some embodiments of the invention relates to a balloon adapted to be removed from a flow reducing implant with a narrowing, through the narrowing and after inflation. In an exemplary embodiment of the invention, the balloon or an outer sheath provided with the balloon comprises a plurality of somewhat flexible wires, which, when retracted through the narrowing and/or through an aperture defined in a delivery catheter, compress together, thereby radially compressing the balloon. Alternatively or additionally, the wires are not axially arranged, for example being spirally arranged, so that when the balloon deflates, the balloon will twist closed.

An aspect of some embodiments of the invention relates to a flow reducing graft-stent comprising a stent body, which may or may not define a narrowed portion and a graft section that is mounted on the stent, for example on its outside or with the stent embedded in the graft, wherein the graft does define a narrowing, for example the graft being generally cone shaped. The graft section is optionally held open using one or more stiffening elements and/or a ring at its narrowed section. Optionally, the graft is impervious to blood flow.

An aspect of some embodiments of the invention relates to a reducing implant mounted inside a support element, for example a stent, a graft or a stent graft. Optionally, this prevents damage of the surrounding vessel by the reducing implant. Alternatively or additionally, this allows the reducing implant to be more easily removed.

An aspect of some embodiments of the invention relates to reducing a vessel diameter using an external element, such as a band or clip. In an exemplary embodiment of the invention, a band is inserted outside the blood vessel and tightened, to reduce the diameter of a narrow and/or a wide section of the flow reducing implant. Such a band may be left in the body, or removed (e.g., be part of a tool), for example, if the flow reducing implant is plastically deformed by the tool. Alternatively or additionally, the band is used to force a collapsing of the vessel on the flow reducing implant, for example is such collapsing did not occur by itself.

An aspect of some embodiments of the invention relates to using a reducing implant in parts of the body other than the coronary veins and/or coronary sinus. In one example, a flow reducing implant is used to reduce flow through one or more veins in the leg resulting in redistribution of blood in the leg and/or triggering of angiogenesis or expansion of existing blood vessels. In another example, a flow reducing implant is used to reduce arterial blood flow to abnormal growths (e.g., tumors), such as growths in the uterus and/or growths in the Liver. A particular property of the liver and the uterus is that these organs receive blood from at least two different sources, while the growths in these organs often receive blood from only one of the sources. In addition, the normal tissue may be able to weather a sharp reduction in blood, while a tumor growth may not.

There is thus provided in accordance with an exemplary embodiment of the invention, a flow reducing implant, comprising:

a flared section adapted to contact a blood vessel wall;

at least one narrowed section continuous with said flared section; and at least one anchor tab that lies generally in a plane of said flared section. Optionally, said implant is formed of a sheet material and wherein said tab is attached to a portion of said flared section that is generally parallel to a wall of said blood vessel, Alternatively or additionally, said anchor tab points axially. Alternatively or additionally, said anchor tab points towards said narrowed section. Alternatively or additionally, the implant comprises at least two opposing anchor tabs. Alternatively or additionally, the implant comprises at least two flared sections, each one with at least one anchor tab.

In an exemplary embodiment of the invention, said implant is plastically deformed to said configuration. Alternatively, said implant self-deforms to said configuration.

In an exemplary embodiment of the invention, said anchor tabs are blunt enough to generally prevent damage to said blood vessel.

There is also provided in accordance with an exemplary embodiment of the invention, a flow reducing implant, comprising:

a flared section adapted to contact a blood vessel wall;

at least one narrowed section continuous with said flared section and adapted to be narrowed after implantation. Optionally, the implant comprises an external ribbon adapted to selectively increasingly constrain said narrowing. Optionally, the implant comprises an impulser adapted to receive signals from outside the body and constrain said ribbon in response.

In an exemplary embodiment of the invention, said ribbon is expandable. Alternatively or additionally, said ribbon is inflatable.

In an exemplary embodiment of the invention, said ribbon is self-expands by absorption.

In an exemplary embodiment of the invention, said ribbon is tearable.

In an exemplary embodiment of the invention, said narrowed section comprises a plurality of engagement points adapted to be engaged, for radial constriction, by a catheter with matching engagers. Alternatively or additionally, said narrowed section is adapted to be selectively widened after implantation.

In an exemplary embodiment of the invention, said narrowed section is inflatable.

In an exemplary embodiment of the invention, said narrowed section is expandable in thickness.

There is also provided in accordance with an exemplary embodiment of the invention, a flow reducing implant, comprising:

a flared section adapted to contact a blood vessel wall;

at least one narrowed section continuous with said flared section; and at least ribbon coupled to said narrowed section and adapted to define at least two discrete expansion states of said narrowed section. Optionally, said at least one ribbon comprises a tearable ribbon. Alternatively or additionally, said at least one ribbon comprises a ribbon with a sliding clasp and a plurality of stop positions defined thereon. Alternatively or additionally, said at least one ribbon comprises a plurality of ribbons, being different in at least one of initial diameter, tear strength and final diameter. Alternatively or additionally, said at least one ribbon comprises a sated ribbon having a first diameter and a second diameter set by said slits being closed or expanded. Alternatively or additionally, said at least one ribbon comprises a cord woven into said narrowed section.

In an exemplary embodiment of the invention, said at least one ribbon lies outside of said narrowed section.

In an exemplary embodiment of the invention, said at least one ribbon is biodegradable.

In an exemplary embodiment of the invention, said at least one ribbon blocks flow through a wall of said narrowed section.

There is also provided in accordance with an exemplary embodiment of the invention, a flow reducing implant, comprising:

a flared section adapted to contact a blood vessel wall;

at least one narrowed section continuous with said flared section, wherein said implant comprises at least one overlapping section, whose overlap changes when said narrowed section is expanded. Optionally, said overlap comprises a plurality of overlapping cut-outs of said implant. Alternatively or additionally, said overlap comprises an overlap of substantially an entire length of said implant.

There is also provided in accordance with an exemplary embodiment of the invention, a flow reducing implant, comprising:

a stent-like element adapted to anchor in a tubular blood vessel; and a flexible cone-shaped nozzle mounted on said stent, said cone shaped nozzle defining a narrowing that substantially reduces a cross-section of blood flow through said sent-like element. Optionally, said nozzle comprises at least one stiffener.

There is also provided in accordance with an exemplary embodiment of the invention, a flow reducing implant, comprising:

an open weave mesh that does not substantially impede blood flow, therethrough; and a layer of graft material mounted on said mesh and defining a narrowed lumen for blood flow therethrough. Optionally, said open weave mesh forms an hourglass shape when expanded in said graft material layer.

There is also provided in accordance with an exemplary embodiment of the invention, a flow reducing implant, comprising:

a flared section adapted to contact a blood vessel wall;

at least one narrowed section continuous with said flared section, wherein said implant is defined by a sheet material with slots and wherein a width of said slots varies over the implant to control an expanded geometry of said implant.

There is also provided in accordance with an exemplary embodiment of the invention, a flow reducing implant, comprising:

a flared section adapted to contact a blood vessel wall;

at least one narrowed section continuous with said flared section, wherein said implant is defined by a sheet material with slots and wherein said slots are arranged in axial lines and wherein said alternating lines have different lengths of slots at a same axial position.

There is also provided in accordance with an exemplary embodiment of the invention, a flow reducing implant for reducing blood flow in a blood vessel, comprising:

a body having a cross sectional dimension; and a restricting element that at least partially encircles a blood vessel. Optionally, said element pierces said blood vessel. Alternatively or additionally, said element comprises a tack or a suture. Alternatively or additionally, said element comprises a band. Optionally, said band comprises a ratchet mechanism that maintains it in position in respect to said vessel. Alternatively or additionally, said band comprises a plurality of expandable slits.

In an exemplary embodiment of the invention, said element comprises one of a clip, clasp and vise. Alternatively or additionally, said element comprises a spiral.

In an exemplary embodiment of the invention, said element comprises an expandable material. Optionally, said element is adapted to expand by expansion pressure from the interior of said blood vessel. Optionally, said implant is adapted to expand in response to expansion pressure of a balloon catheter.

There is also provided in accordance with an exemplary embodiment of the invention, a method of treating abnormal growth: in the body, comprising:

determining a source artery for the growth; and inserting a flow reducing implant with an adjustable configuration into the determined artery, such that flow to the growth is reduced. Optionally, said growth is extant in an organ that is fed from multiple source arteries. Alternatively or additionally, said growth is fed by a single source artery. Alternatively or additionally, said growth comprises a leiomyoma. Alternatively or additionally, said growth comprises a malignant tumor. Optionally, said tumor is a liver tumor. Alternatively or additionally, said tumor is an encapsulated tumor.

There is also provided in accordance with an exemplary embodiment of the invention, a method of treating blood flow problems in a limb, comprising:

identifying at least one vein that if flow in the vein is reduced is expected to reduce the blood flow problem; and inserting a flow reducing implant into the determined vein. Optionally, said vein is a deep vein. Alternatively, said vein is a surface vein.

There is also provided in accordance with an exemplary embodiment of the invention, a flow reducing implant comprising:

an outer generally tubular section adapted to be inserted in a blood vessel; and an insert adapted to lodge in said tubular section, said insert designed to reduce blood flow passing through the blood vessel. Optionally, said generally tubular section is designed to reduce blood flow passing therethrough. Alternatively or additionally, said insert comprises a funnel shaped insert. Alternatively or additionally, said generally tubular section is designed to not reduce blood flow passing therethrough. Alternatively or additionally, said generally tubular section comprises a plurality of opening in its wall and wherein said insert comprises a plurality of opening in its wall. Optionally, said insert and said tubular section are rotationally alignable to modify an alignment of said pluralities of openings with each other.

There is also provided in accordance with an exemplary embodiment of the invention, a method of reducing flow in a blood vessel, comprising:

selecting a location in the vessel to narrow;

inserting a flow reducing implant into the blood vessel at the location; and mounting a restricting element on said vessel at the location and over said flow reducing implant. Optionally, said restricting element reduces an inner diameter of said flow reducing implant. Optionally, said method comprises removing said restricting element.

BRIEF DESCRIPTION OF THE DRAWINGS

Non-limiting embodiments of the invention will be described with reference to the following description of exemplary embodiments, in conjunction with the figures. The figures are generally not shown to scale and any measurements are only meant to be exemplary and not necessarily limiting. In the figures, identical structures, elements or parts that appear in more than one figure are preferably labeled with a same or similar number in all the figures in which they appear, in which:

FIGS. 4C-4D are a plan layout and isometric view, respectively, of a slit-type flow reducing implant with a smooth rim, in accordance with an exemplary embodiment of the invention;

FIGS. 7A and 7B are a plan view and an isometric view of a flow reducing implant embodiment with anchors, in accordance with an exemplary embodiment of the invention;

FIGS. 9A-9G are embodiments of flow reducing implant, in accordance with exemplary embodiments of the invention;

FIGS. 10A-10B are an isometric view and detail, respectively, of a ringed mesh-type flow reducing implant embodiment, in accordance with an exemplary embodiment of the invention;

DETAILED DESCRIPTION OF EXEMPLARY EMBODIMENTS

Figure 1:
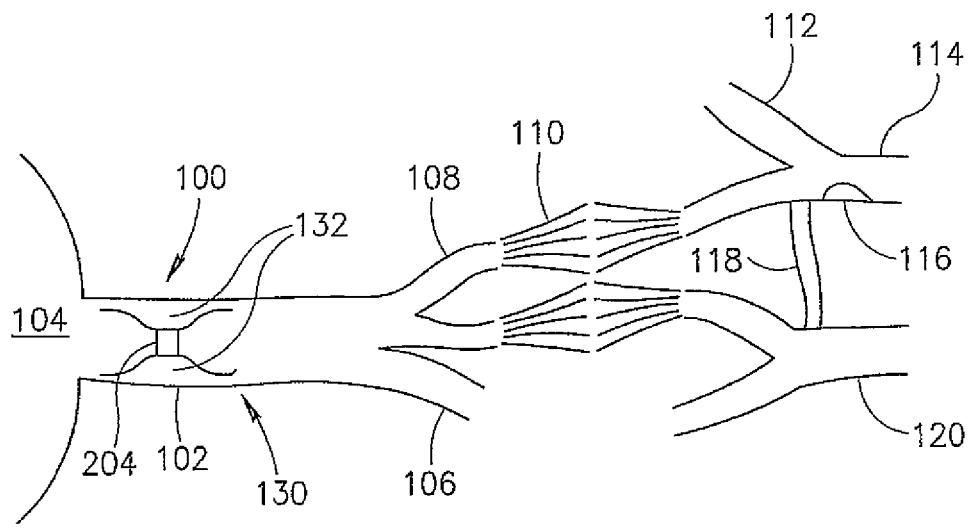
FIG. 1 is a schematic showing of a flow reducing implant installed in a coronary sinus vein, in accordance with an exemplary embodiment of the invention.

FIG. 1 is a schematic showing of a flow reducing implant 100 installed in a coronary sinus vein 102, in accordance with an exemplary embodiment of the invention. Coronary sinus 102 drains a plurality of cardiac veins 106 into a right atrium 104. The cardiac circulation is generally hierarchical and comprises of stages of reducing (or increasing) diameter. Thus, veins 106, in turn, drain a plurality of thin venules 108, which, after a few stages, drain a plurality of capillaries 110. Capillary 110 is fed by a plurality of arterioles 112, which, after a few stages, are fed by a plurality of coronary arteries 114 and 120. A stenosis 116 is shown in a coronary artery 114. While the cardiac circulation is generally hierarchical, some connection exists between different branches. Occasionally, the existence of stenosis 116 will cause a collateral connection 118 to spontaneously form (or widen an existing connection) between coronaries 114 and 120, bypassing stenosis 116.

In some cases, however, this spontaneous formation does not occur. In an exemplary embodiment of the invention, a flow reducing implant 100 is placed in coronary sinus 102 and has a narrowing significant enough to encourage the formation of collateral connection 118. It is hypothesized that collateral connection 118 is caused by an increase in venous blood pressure, which, in turn, increases the pressure in the capillaries and/or causes retro-flow in the capillaries and/or causes drainage of the capillaries directly into the heart. However, even if this hypothesis is incorrect, several studies, that included numerous experiments and actual procedures have shown that constriction of coronary sinus 102 will generally cause the formation of collateral circulation and/or otherwise improve the condition of patients with blocked coronary arteries. Alternative or additional hypotheses that are optionally used to select the constrictive effect of flow reducing implant 100 include:

(a) Flow reducing implant 100 increases the pressure in the coronary capillaries, thus increasing perfusion duration.

(b) An increase in resistance of the venous system causes redistribution of blood flow in coronary arteries.

(c) An increase in resistance of venous system increases intra-myocardial perfusion pressure and/or intra-myocardial pressure.

(d) Increasing the arterial diastolic pressure (by restricting venous drainage) causes the arterial auto-regulation to start working again, for example, such an auto regulation as described in Braunwald "Heart Disease: A Textbook of Cardiovascular Medicine", 5th Edition, 1997, W.B. Saunders Company, Chapter 36, pages 1168-1169.

It should be noted that the selection of flow reducing implant 100 may be made to achieve one or more of the above suggested effects, optionally to a desired degree and/or taking into account safety issues, such as allowing some drainage and maximum pressure allowed by the coronary venous drainage system.

Figure 2:
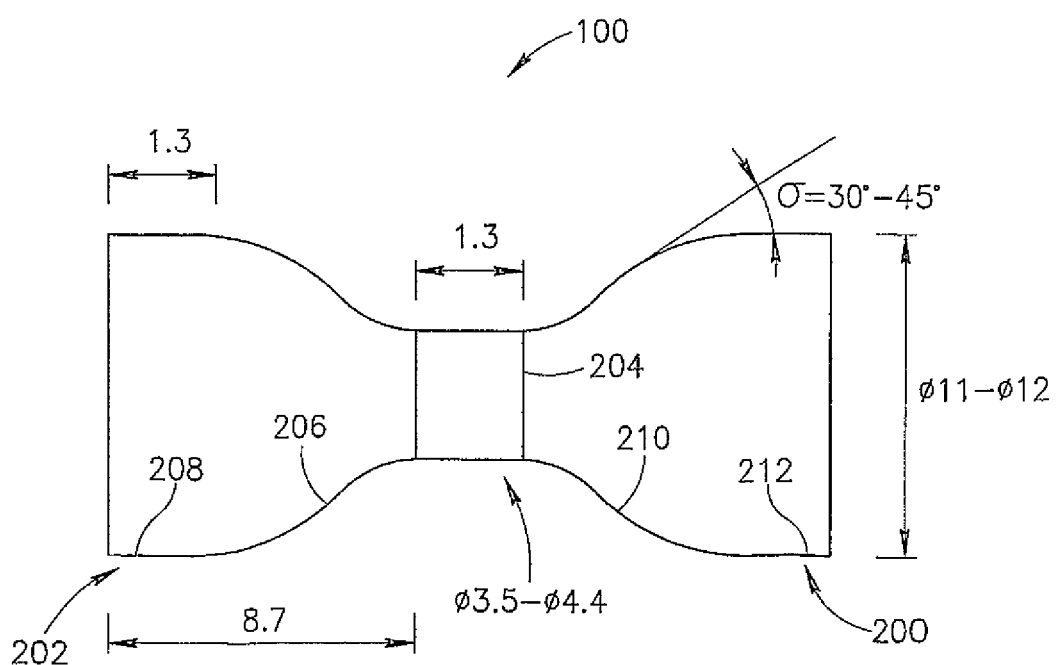
FIG. 2 is a schematic side view of a flow reducing implant, in accordance with an exemplary embodiment of the invention.

FIG. 2 is a schematic side view of flow reducing implant 100, in accordance with an exemplary embodiment of the invention. Flow reducing implant 100 comprises a narrowed section 204 and at least one flared section 200 (and 202) leading into narrowed section 204. Section 200 (and 202) includes sections 210 and 206 that are inclined relative to the wall of coronary sinus 102 and sections 212 and 208 that are parallel to the wall.

In the exemplary embodiment and measurements shown, flow reducing implant 100 is expandable and shortens somewhat during expansion: having a length of 20 mm before expansion and about 18.8 mm after expansion. Optionally, a non-shortening design is used, for example a mesh as in peristaltic stents, such as described in U.S. Pat. No. 5,662,713, the disclosure of which is incorporated herein by reference. An exemplary material thickness is 0.15 mm, however, thinner or thicker materials may be used. Other exemplary lengths are 5 mm, 12 mm, 24 mm, 35 mm 45 mm and any smaller, intermediate or larger size. The length is optionally selected to match a physiological size of the target vein (e.g., length and curves) and/or to ensure good contact with vein walls. The length of narrowed section 204 may be, for example, 0.5 mm, 1 mm, 2 min, 3 mm, 5 mm or any smaller, intermediate or larger length, for example selected to achieve desired flow dynamics An exemplary inner diameter of the flared sections is between 2 mm and 30 mm, for example, 5 mm, 10 mm, 15 mm, 20 mm or any larger, smaller or intermediate diameter, for example selected to match the vein diameter. The inner diameter of the narrowed section may be, for example, 1 mm, 2 mm, 3 mm, 5 mm, 10 mm or any smaller, larger or intermediate diameter, for example selected to achieve desired flow dynamics and/or a pressure differential across the flow reducing implant.

In an exemplary embodiment of the invention, the ratio between the cross-section of narrowed section 204 and the flares of flow reducing implant 100 is 0.9, 0.8, 0.6, 0.4, 0.2 or any larger, smaller or intermediate ratio, for example selected to achieve desired flow dynamics and/or a pressure differential across the flow reducing implant.

While a circular cross-section is shown, other cross-sections may be used, for example, polygonal and ellipsoid. A potential advantage of non-circular cross-sections is that the implant is less likely to migrate axially and/or rotate. Alternatively or additionally, the outside of the flow reducing implant is roughened and/or otherwise adapted to adhere to the vein wall. The cross-section shape and/or orientation optionally changes along the length of flow reducing implant 100.

Figure 3A:
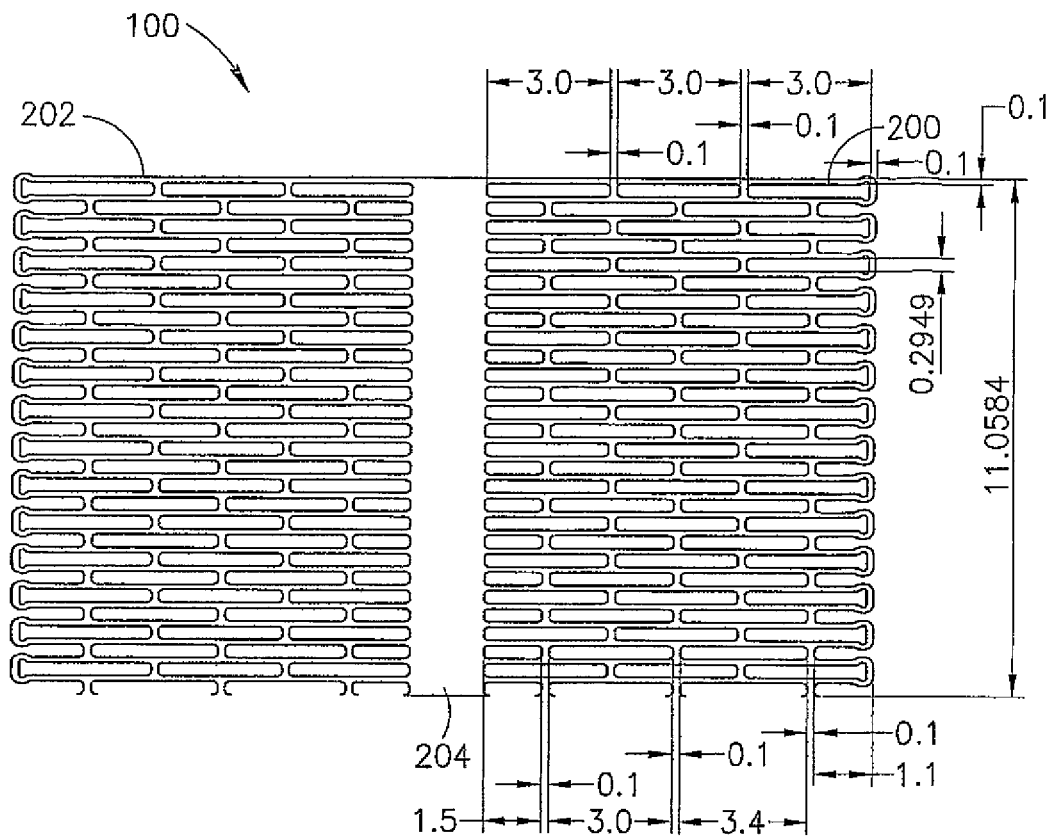
FIGS. 3A-3B are plan layouts of a slit-type flow reducing implant, in accordance with an exemplary embodiment of the invention.
Figure 3B:
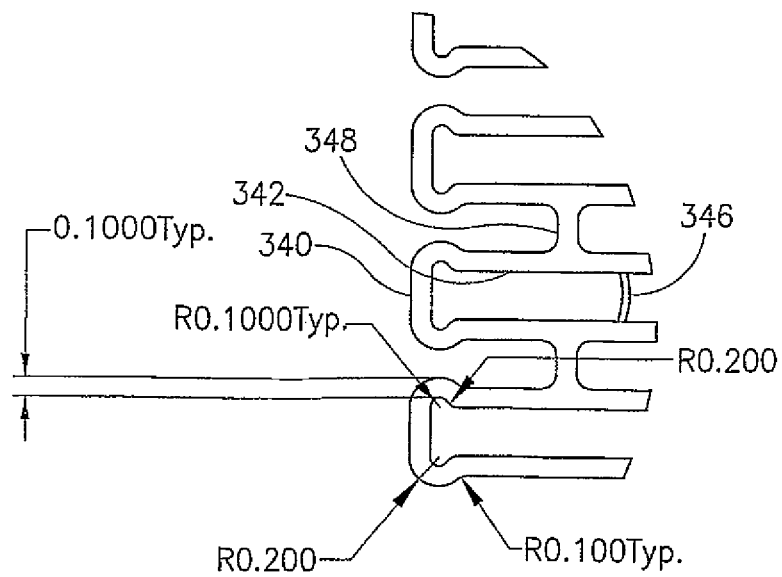

FIG. 3A is a plan layout of a slit-type flow reducing implant and FIG. 3B is a detail of FIG. 3A, in accordance with an exemplary embodiment of the invention. In this plan layout, the ends of sections 200 and 202 are caused to be parallel to the vessel wall when flow reducing implant 100 is expanded.

In an exemplary embodiment of the invention, the outside flare of flow reducing implant 100 is defined by sections 340, 342 and 344, shown in FIG. 3B. Optionally, the total length of these sections defines the maximum flare length. Alternatively or additionally, the bending areas in and between these sections define the relative force required to expand the flare region relative to the area near the rim. If the rim region is more difficult to expand and/or is expanded less than the adjacent regions, the expansion of flow reducing implant 100 will tend to cause the rim to be bent in, or at least not flare out. Alternatively, in a self-expanding flow reducing implant, the existence of sections 340, 342 and 344 can be used to determine the final shape of the flare. Optionally, additional sections 346 are provided around the circumference of flow reducing implant 100, which define outer slits in flow reducing implant 100, which outer slits may have a maximum expansion that is the same or smaller than that nearby (axially inwards) slits. This design can also be used to control the shape of the flare.

In an exemplary embodiment of the invention, a flow reducing implant is characterized by this maximum diameter, which may be used, for example, for selecting a particular flow reducing implant to match a patient. Optionally, during expansion, the balloon is aligned with flow reducing implant 100 so that it only contacts the flare region or only contacts the non-flare regions of flow reducing implant 100.

Figure 3C:
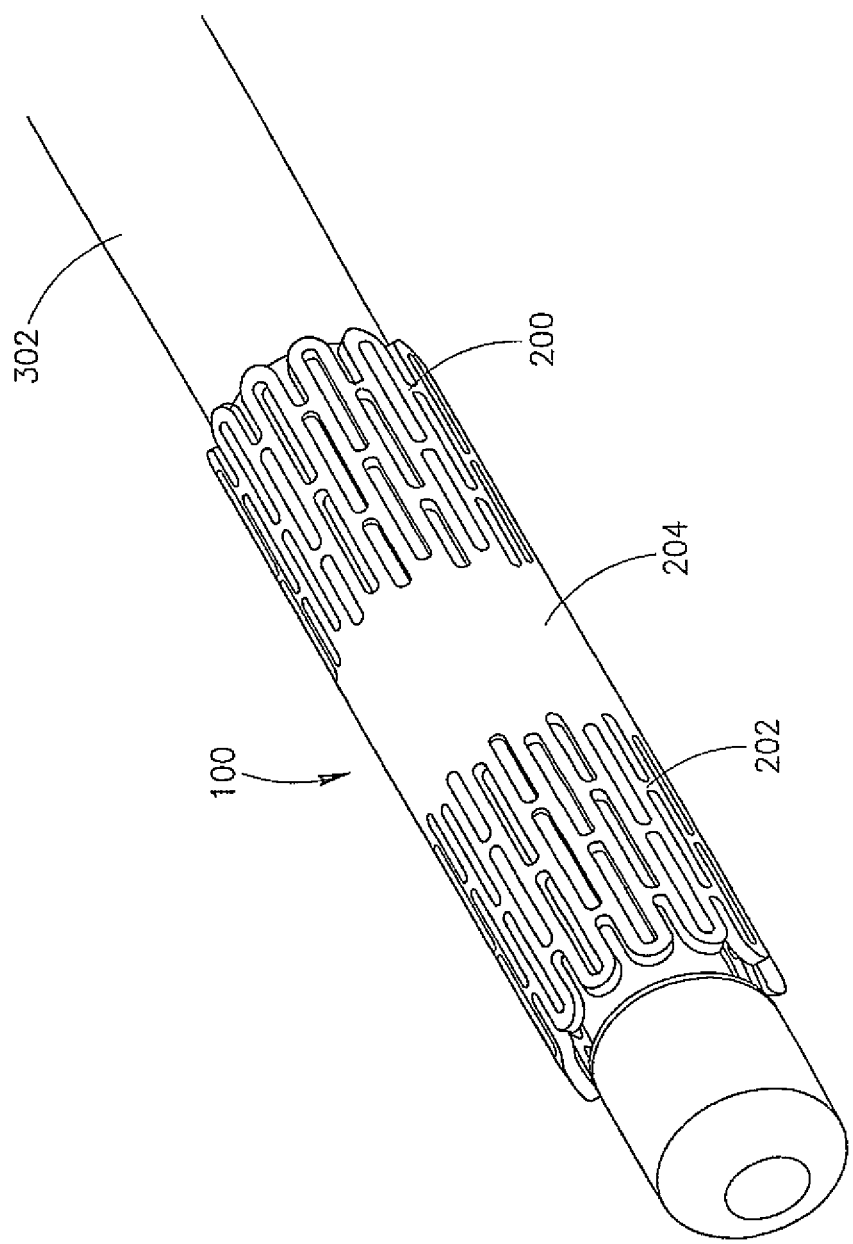
FIG. 3C is an isometric vies of the flow reducing implant of FIG. 3A mounted on a balloon catheter delivery system, in accordance with an exemplary embodiment of the invention.

FIG. 3C is an isometric view of flow reducing implant 100 (FIG. 3A), mounted on a balloon catheter delivery system 302, in accordance with an exemplary embodiment of the invention.

In an exemplary embodiment of the invention, flow reducing implant 100 is formed by cutting out of a sheet of metal or a tube, for example, using laser, water cutting, chemical erosion or metal stamping (e.g., with the result being welded to form a tube). Alternatively, flow reducing implant 100 is woven (e.g. of metal or plastic fiber), for example, using methods as well known in the art. Optionally, narrowed section 204 is made using a different method from flared sections 200 and 202, for example, the flared sections being woven and the narrowed section being cut from sheet metal. In an alternative embodiment of the invention, flow reducing implant 100 includes with a constraining ring that prevents the expansion of narrowed section 204. Optionally, the restraining ring is plastically expandable, possibly under a higher pressure than the rest of flow reducing implant 100, which may be plastically deformable or self-expanding. Alternatively or additionally, the restraining ring is selected to set the desired degree of narrowing, and then mounted on a flow reducing implant, a stent or a stent graft, for implantation. In a sleeve flow reducing implant (FIG. 9G) a similar effect may be achieved by suturing the stent graft.

Upon attaining its destination, a standard balloon catheter with a single expansion area, for example the Fox Catheter™ by Jomed, inc., may be used to encourage the implant to attain its contoured shape. As the balloon presses against lumen of the implant, the narrowed section is prevented from expanding while flared sections 200 and 202 expand under pressure. Various methods for preventing the narrow section from expanding are described below, for example, providing different mechanical properties, different designs or additional elements at the narrowed sections relative to the non-narrowed sections.

In an alternative embodiment, flow reducing implant 100 is cut out of a sheet and then spirally twisted around a mandrel to form the shape of flow reducing implant 100. Alternatively, flow reducing implant 100 is cut out of a tube, with the flared parts being spiral cuts and the narrowing part being a ring cut. Alternatively, flow reducing implant 100 is formed as a coil spring, with axially varying relaxation positions.

In an exemplary embodiment of the invention, flow reducing implant 100 is adapted for use in a coronary sinus or other coronary vein or other veins having non-muscular walls. Veins are typified by having a low degree of elasticity and being relatively sensitive to tears (as compared to arteries). In one example, the edges of flow reducing implant 100 are curved inwards or curled, for example as shown by reference 130 in FIG. 1, Alternatively or additionally, the edges are folded back and/or smoothed to remove sharp edges. Alternatively, the parallel sections 208 and 212 (FIG. 2) are made long enough to support flow reducing implant 100 without harming coronary sinus 102. Alternatively or additionally, flow reducing implant 100 or at least a larger diameter portion thereof, is made soft enough and/or with a low spring constant, to prevent flow reducing implant 100 from applying too much pressure on the coronary flow reducing implant wall. Alternatively or additionally, the flares of flow reducing implant 100 are coated with a biologically inert flexible coating, for example, a soft silicone elastomer or another soft plastic or rubber material such as Latex, Teflon and/or Polyurethane (for example Angioflex, a biologically inert polyurethane plastic).

Figure 4A:
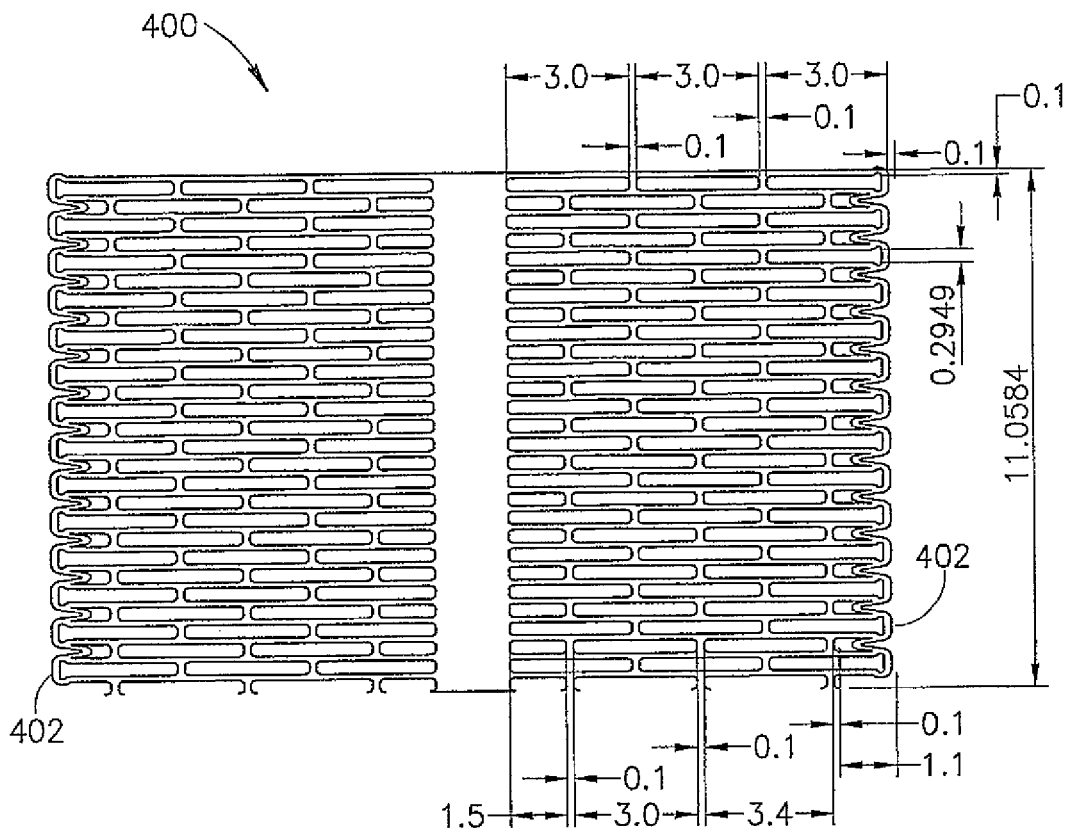
FIGS. 4A-4B are plan layouts of a slit-type flow reducing implant, in accordance with an exemplary embodiment of the invention.
Figure 4B:
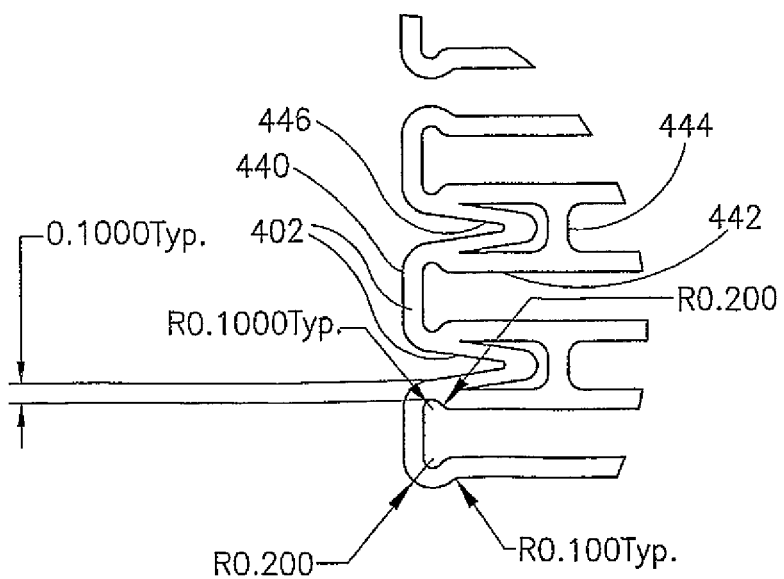

FIGS. 4A-4B are plan layouts of slit-type flow reducing implant 100, in accordance with an exemplary embodiment of the invention. In FIG. 4B, rim 402 is defined by sections 440 and 446. As shown, these sections are designed to provide a relative smooth rim, possibly with small amounts of distortion (so rim 402 remains smooth) where the sections connect to sections 442 and 444. Together, sections 442, 444 and 446 define outer slits for rim 402.

Patients that are candidates for an angiogenesis-promoting procedure may have significant vascular compromise of the coronary circulation with constriction and/or lack of flow in one or more coronary arteries that supply blood to the coronary tissue. An invasive surgical procedure, even to percutaneously introduce and/or position a reducing implant 100 into the coronary sinus, may trigger a cardiovascular accident with untoward sequella. Hence, averting and/or limiting the amount of time that the vasculature is invaded, for example, during use of a balloon catheter is desirable in some individuals.

Figure 4C:
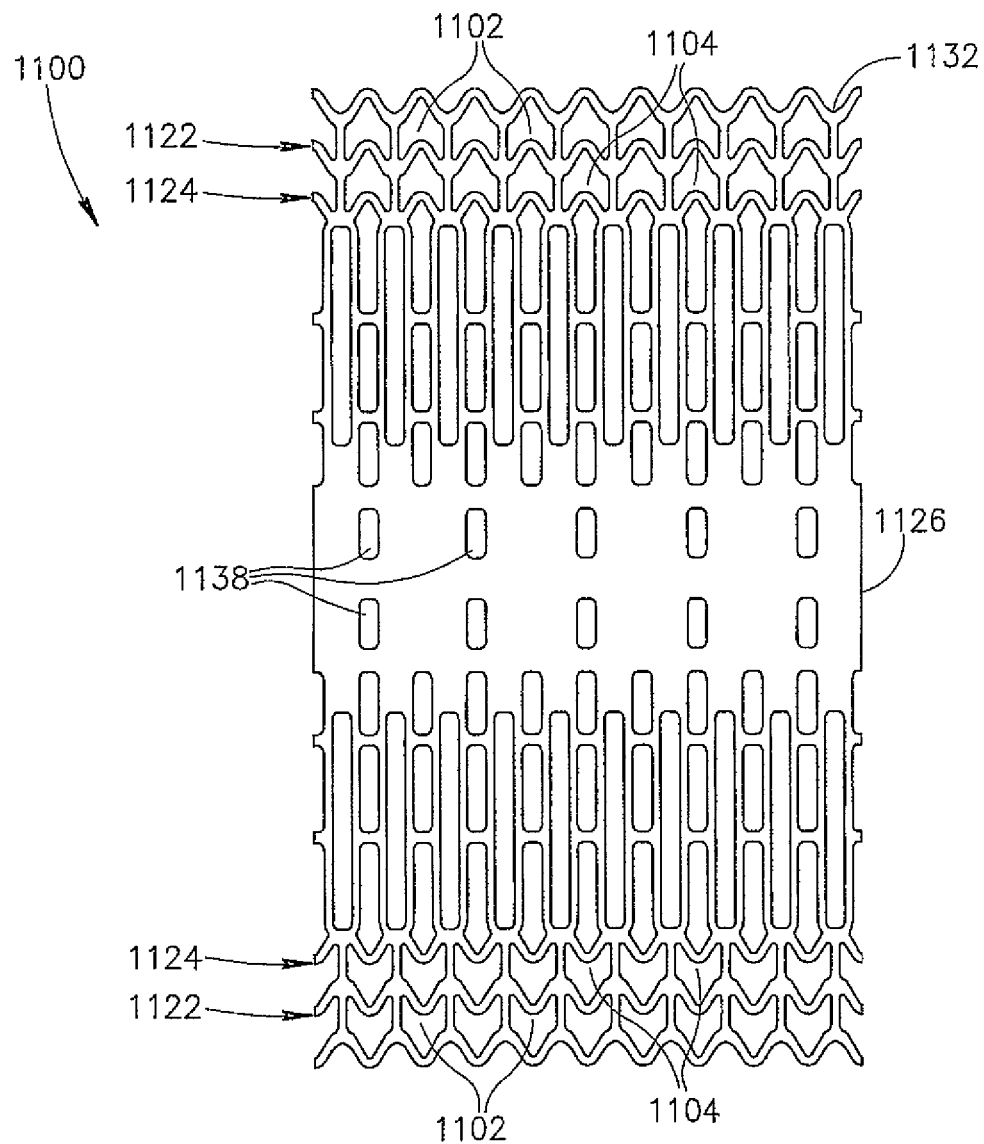

FIGS. 4C-4D are a plan layout and isometric view, respectively of a slit-type flow reducing implant 1100 with a smooth rim, in accordance with an exemplary embodiments of the invention.

In an exemplary embodiment of the present invention, slit-type flow-reducing implant 1100 comprises shape memory materials that automatically achieve a final configuration state upon exiting, for example, a delivery catheter or sheath, thereby averting the use of a balloon catheter for initial installation of slit-type flow-reducing implant 1100. Alternatively, a balloon expended material, for example one that plastically deforms by expansion, may be used.

In an exemplary embodiment, slit-type coronary flow-reducing implant 1100, shown in a plan view in FIG. 4C, contains preformed slits 1102, in accordance with an exemplary embodiment of the invention. Slits 1102 (and optionally a set of slits 1104 in a second or further row) define a row 1122 (and a row 1124) along an outer edge 1132 of slit-type flow-reducing implant 1100 that, in the unexpanded state comprise at least one edge 1132 that has a wavy configuration. Upon expansion, for example shown in FIG. 4D, edge 1132 becomes smooth while slits 1102 assume a rectangular appearance, with edge 1132 transverse to a slit 1126, for example. In an exemplary embodiment of the invention, the slits of the rim are wider than the slits of the rest of implant 1100, thereby affecting its final expanded configuration.

In an exemplary embodiment of the present invention, slit-type coronary flow-reducing implant 1100 is transferred to its deployment site in coronary sinus using a guide sheath without accompaniment by a balloon catheter. As slit-type coronary flow-reducing implant 1100 reaches its destination and exits its guide sheath, coronary flow-reducing implant 1100 automatically expands into its final shape, shown in FIG. 4D. In this manner, slit-type coronary flow-reducing implant 1100 does not require manipulation and/or expansion using, for example, a balloon catheter.

Alternatively or additionally, a balloon catheter may be used to facilitate expansion of slit-type flow-reducing implant 1100, for example, when it is made of materials that do not automatically attain a memorized shape. In an exemplary embodiment, rows of slits 1122 and/or 1124 have lengths and/or orientations that promote flow-reducing implant 1100 to form into a final shape under pressure of a balloon catheter, therefore, installing with a minimal amount of time and/or stress to the surrounding tissue.

In an exemplary embodiment, slit-type coronary flow-reducing implant 1100 is designed to alter its shape in response to manipulation and/or expansion following installation. In an exemplary embodiment, slits 1138 expand so that a narrow passage 1168 automatically attains a first diameter during installation. In an exemplary embodiment, following installation of slit-type coronary flow-reducing implant 1100, a balloon catheter is introduced into narrow passage 1168 and inflated to press radially outward on narrow passage 1168. In an exemplary embodiment, a pressure, for example, of between 7 and 8 atmospheres or less than 7 or greater than 8 atmospheres, depending, for example on the stiffness of the component materials, causes expansion slits 1138 to expand to a larger cross section. This causes narrow section 1168 to have a larger diameter than it had immediately following installation.

While not shown, some of the slits, for example slits 1138 may be oblique, thus possibly requiring a different degree of force to expand and/or providing a twisting of the deployed implant. Providing opposing oblique slits may be used to providing a shortening of the implant.

In an exemplary embodiment, when flow-reducing implant 1100 is installed, little or no blood migrates through the walls of narrow passage 1168 and/or a flare 1160 to contact the walls of the coronary sinus. This, for example, is achieved by a narrow configuration of the slits. Alternatively or additionally, the length of the slits decreases near narrowing 1168.

In an exemplary embodiment, to achieve limitation and/or cessation of blood flow through the implant walls, the slits (e.g., not only slits 1102 and 1104 at the rim) are increased in number, while their width is reduced. The viscosity of the blood impedes its flow through the decreased width of the slits while the increased number of slits may fosters expansion of implant 1100. This may result in a net reduction in blood flow through the implant walls.

Alternatively or additionally, the slit width may be used to help define the device geometry. For example, slits (actually spaces) 1104 are wider than the other slits. If, for example, slits 1104 are made wider than slits 1102, a curved in rim may result.

Also shown is an optional design in which slits are arranged in alternating rows of long and short slits. Alternatively or additionally and as shown, the size and/or density of slits is larger near the rims than near the center of implant 1100. Alternatively or additionally and as shown, the length of the slits increases as a function of the distance from narrowing 1168.

As shown in FIG. 4D, the material of implant 1168 is distorted by the expansion. Alternatively or additionally, the slits are distorted and the material is distorted to conform to these distortions. For example, in one implantation, the short axial slit nearest the rim achieves a trapezoid rather than rectangular shape. In general, the expanded configurations are idealized, with an actual expanded shape possibly including step-like distortions caused by the discrete pattern of the slits in the implant.

Figure 5:
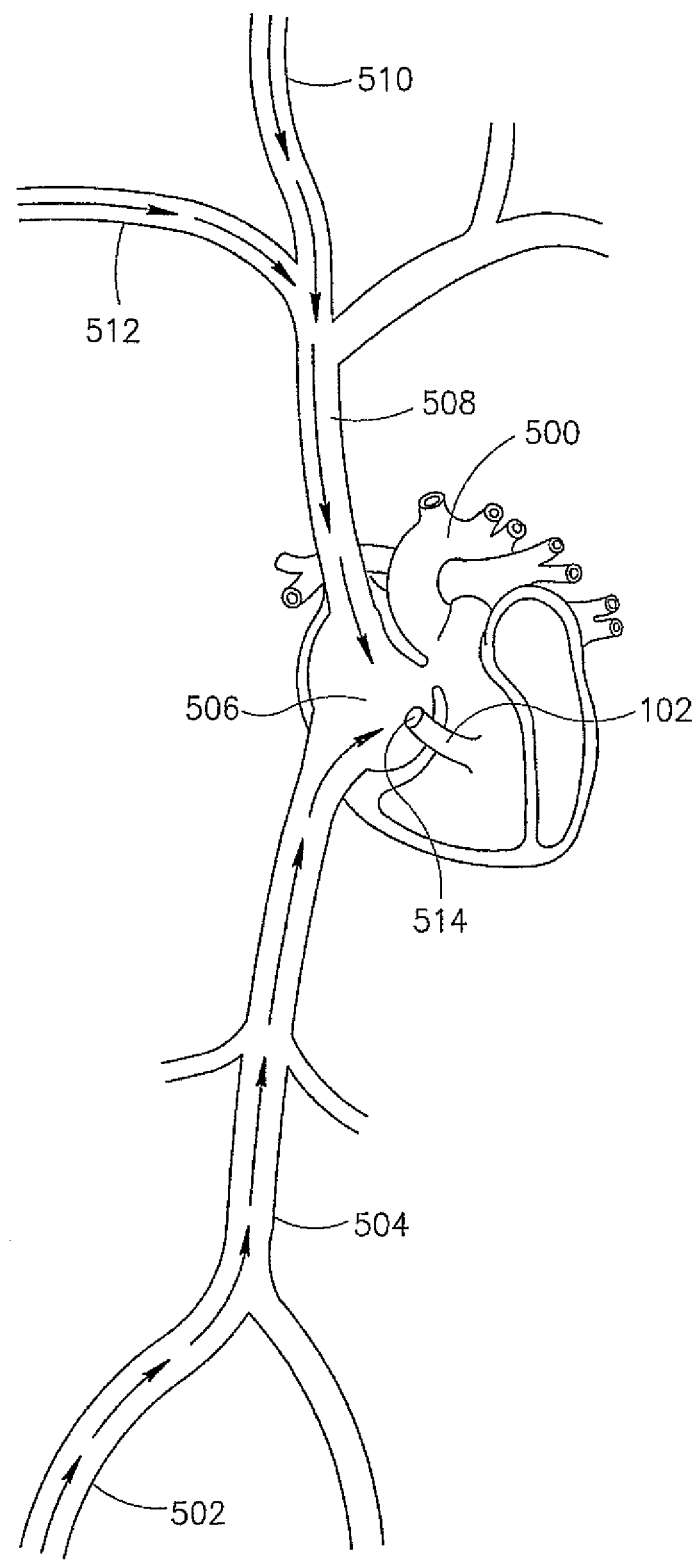
FIG. 5 is a vascular path to a coronary sinus, in accordance with an exemplary embodiment of the invention.

FIG. 5 shows a vascular path to coronary sinus 102, in accordance with an exemplary embodiment of the invention. Desirably, flow reducing implant 100 is implanted using a trans-vascular approach, for example, from the venous system or by crossing through an intra-chamber wall in the heart. In an exemplary embodiment of the invention, the delivery system is inserted through a jugular vein 510 or a subclavian vein 512 to a right atrium 506 of a heart 500 via a superior vena cava 508 and/or a femoral vein 502, via an inferior vena cava 504. Once in right atrium 506, the delivery system is guided (e.g., through a sharp bend) to an opening 514 into coronary sinus 102. In some patients, a valve exists at the entrance to coronary sinus 102.

Figure 6A:
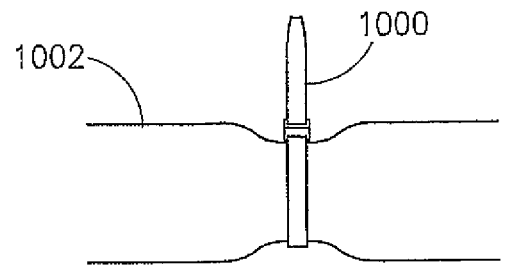
FIGS. 6A-6C are three exemplary vise embodiments that reduce flow through a blood vessel, in accordance with an exemplary embodiment of the invention.
Figure 6B:
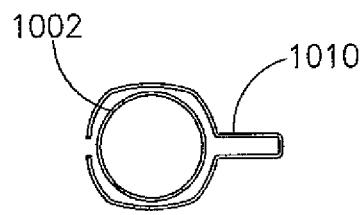
Figure 6C:
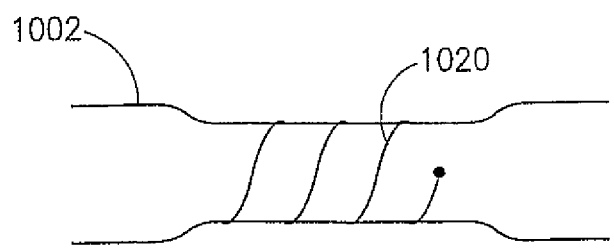

FIGS. 6A-6C are three exemplary vise embodiments, 1000, 1010 and 1020, that reduce flow through a blood vessel 1002, and are applied from outside the blood vessel, in accordance with exemplary embodiments of the invention. Vise 1000 (FIG. 6A) is a band having any ratchet mechanism for preventing opening as known in the art; vise 1010 is a clip-like clasp; and vise 1020 is an elastic spiral.

In an exemplary embodiment of the invention, the band, clip and/or spiral are distortable. In one example, if the narrowing is too great, a balloon catheter can be inserted into the vessel and expanded, causing the spiral, clip and/or band to distort. In one example, the band comprises a plurality of slits (e.g., as in FIG. 8A), that accommodate such distortion.

Figure 6D:
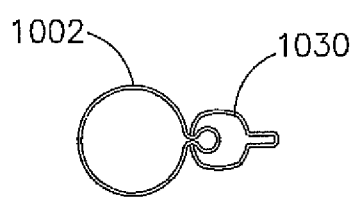
FIGS. 6D-6F show three exemplary clamp embodiments that reduce blood flow through vessel 1002, in accordance with exemplary embodiments of the invention
Figure 6E:
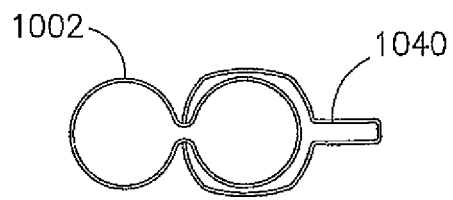
Figure 6F:
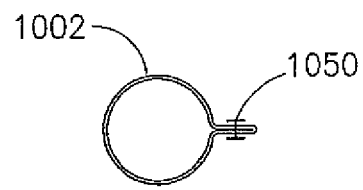

FIGS. 6D-6F show three exemplary clamp embodiments, 1030, 1040 and 1050, that reduce blood flow through vessel 1002, in accordance with exemplary embodiments of the invention. Clamp 1030 is a clip that shuts down part of the cross-section of vessel 1002; clamp 1040 is also a clip, that only distorts the cross-section of vessel 1002; and clamp 1050 is a tack (or suture) that transfixes a part of vessel 1002. Non-piercing clips are optionally designed to have rounded tip and/or non-meeting tips to reduce danger of piercing.

Figure 6G:
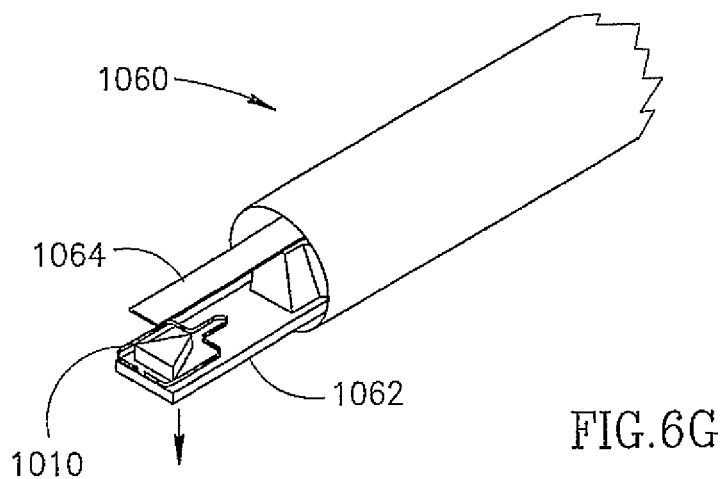
FIG. 6G illustrates an exemplary endoscopic tool for releasing a blood vessel reducing clip, in accordance with an exemplary embodiment of the invention.

FIG. 6G illustrates an exemplary endoscopic tool 1060 for releasing blood vessel reducing clip 1010, in accordance with an exemplary embodiment of the invention. Clip 1010 is held between a flat plate 1060 and a Trans-axially movable arm 1062 with a broadened tip. Retracting arm 1062 towards tool 1060 causes the clip to open and moving arm 1062 in a Trans-axial direction frees the clip. Various other clip deployment mechanisms (for plastic and elastic materials) are known in the art and may be used. In an exemplary embodiment of the invention, the procedure is performed through a key hole and using a working channel or a different keyhole to provide visual verification of the procedure. Alternatively or additionally, radiological verification may be provided. Various implants are known in the art for applying bands to blood vessel and may be used for the example of FIG. 6A as well.

Flow-reducing implants 1000, 1010, 1020, 1030, 1040 and/or 1050 may be deployed on vessel 1002. Alternatively, these implants may be deployed onto tissue enclosing vessel 1002. For example, in the case of the coronary sinus, the implant may be deployed onto (and/or piercing through) a pericardium and/or cardiac muscle tissue.

Figure 7A:
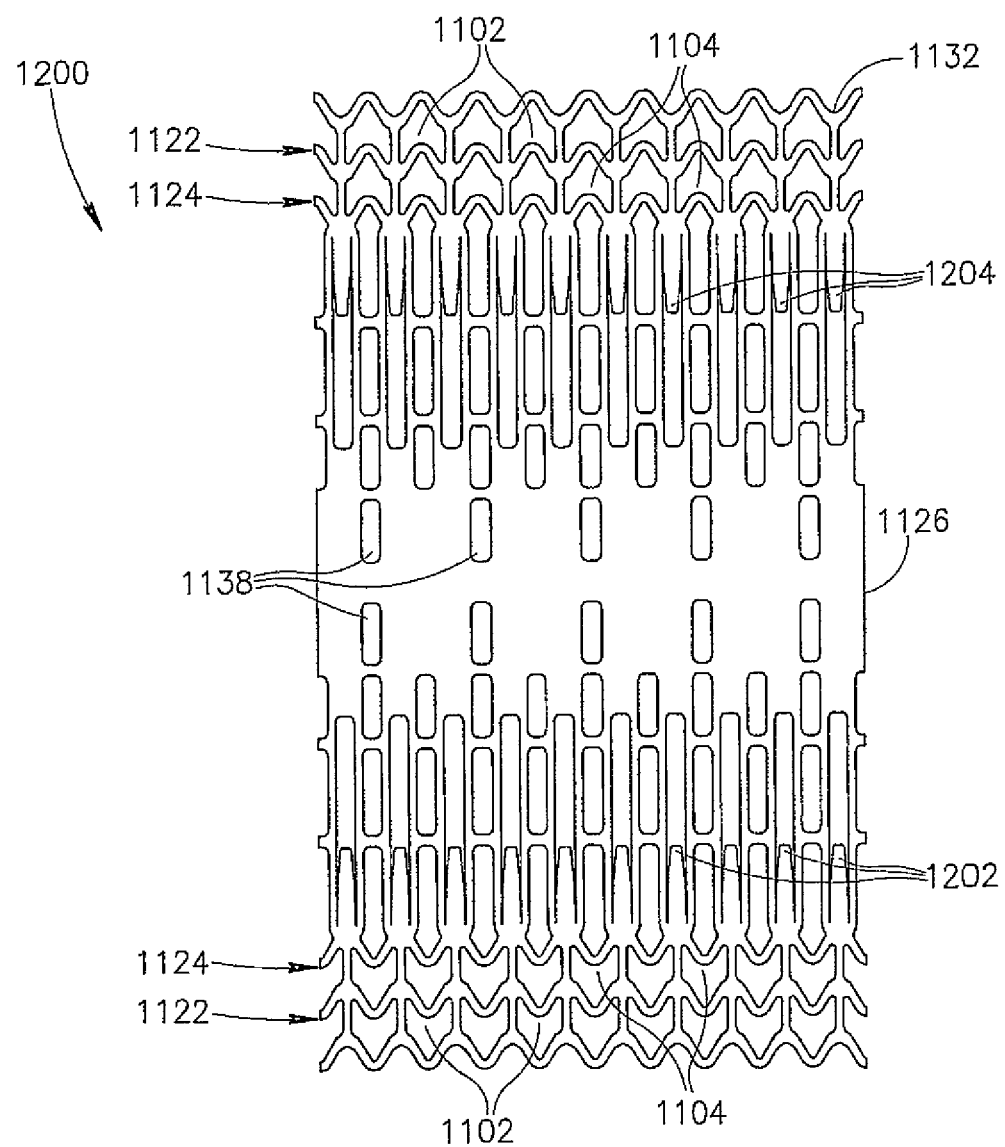

FIGS. 7A and 7B are a plan view and an isometric view of a flow reducing implant 1200 with anchors, in accordance with an exemplary embodiment of the invention.

In an exemplary embodiment of the present invention, an anchor-type flow-reducing implant 1200 comprises at least one anchor 1202 that prevents motion of anchor-type flow-reducing implant 1200 in relation to a blood vessel. Optionally, at least one anchor 1202 and/or 1204 are parallel to the blood vessel and catch on the tissue of the blood vessel to prevent displacement of anchor-type implant 1200. While the anchors are shown as flat, blunt and axial tabs, other designs may be used, for example, sharp, curled and/or oblique to the vessel axis.

Alternatively or additionally, implant 1200 comprises one of row of anchors 1202 and/or row of anchors 1204 that prevent motion. In an exemplary embodiment, anchors 1202 and/or 1204 are substantially parallel to the longitudinal axis of implant 1200 when it is in the non-expanded state and in the expanded state, shown in FIG. 7B. In an exemplary embodiment of the invention, this parallel layout is achieved by the anchors being attached only to the rims and not the flaring section of the implant. thus, they tend to stay in the plane of the rim, which may be, for example parallel to the blood vessel wall or even pointing the anchors towards the wall (e.g., if the rim is curled in)

In an exemplary embodiment, anchor 1202 and/or 1204 are connected to anchor-type flow-reducing implant 1200 and protrude from its surface to into the surrounding tissue with a pressure sufficient to prevent motion of the implant without causing tissue irritation. This can be important in veins, for example, that have less thickness than comparable arteries.

In an environment where the vascular tissue is not uniform in diameter and/or tends to stretch, for example in the coronary sinus, or in other situations, anchors that press with greater force or are pre-stressed to a greater non-parallel angle into the surrounding tissue may be desirable. In an exemplary embodiment, anchor 1202 and/or 1204 are designed for such a vessel and press radially outward from the wall of anchor-type flow-reducing implant 1200, against the surrounding tissue.

The design of anchor-type flow-reducing implant 1200 includes anchors 1202 that have a free end that is not attached to narrow passage 1168 and, for example, blunt to avert tissue irritation. In an exemplary embodiment, one or more deployed anchors 1202 are parallel to a longitudinal axis 1210 of anchor-type flow-reducing implant 1200, and point towards one or more anchors 1204.

At a merging point of two vessels, the vessels may form a lumen with an ellipsoid cross section. An anchor-type flow-reducing implant with anchors 1202 and/or 1204 that point toward one another may tend to migrate laterally and/or displace to one side of the other of the lumen. In an exemplary embodiment, anchors 1202 and/or 1204 of anchor-type flow-reducing implant 1200 may be configured to compensate for not-cylindrical implantation environments.

For example, anchors 1202 and/or 1204 may be configured to point in a substantially perpendicular direction to longitudinal axis 1210 of anchor-type flow-reducing implant 1200, thus tending to prevent lateral movement of implant 1200. In still another embodiment, anchors 1202 and/or 1204 may be connected to an edge 1232 and pointing away from anchors 1204 that are connected to an edge 1234. In this way, anchors 1202 and/or 1204 press into tissue at the edge of the implant that is stronger and/or exhibits a more uniform circumference.

Alternatively or additionally, anchors 1202 and/or 1204 can be oriented in an oblique direction oblique to a transverse axis 1220 and/or longitudinal axis 1210, for example, to prevent migration in an environment where there is strong flow force of the blood stream that tends to exert force and displace implant 1200.

While the anchors are shown cut out of the long slits, alternatively or additionally, the anchors may be cut out of short slits, for example a slit 1125.

Figure 8A:
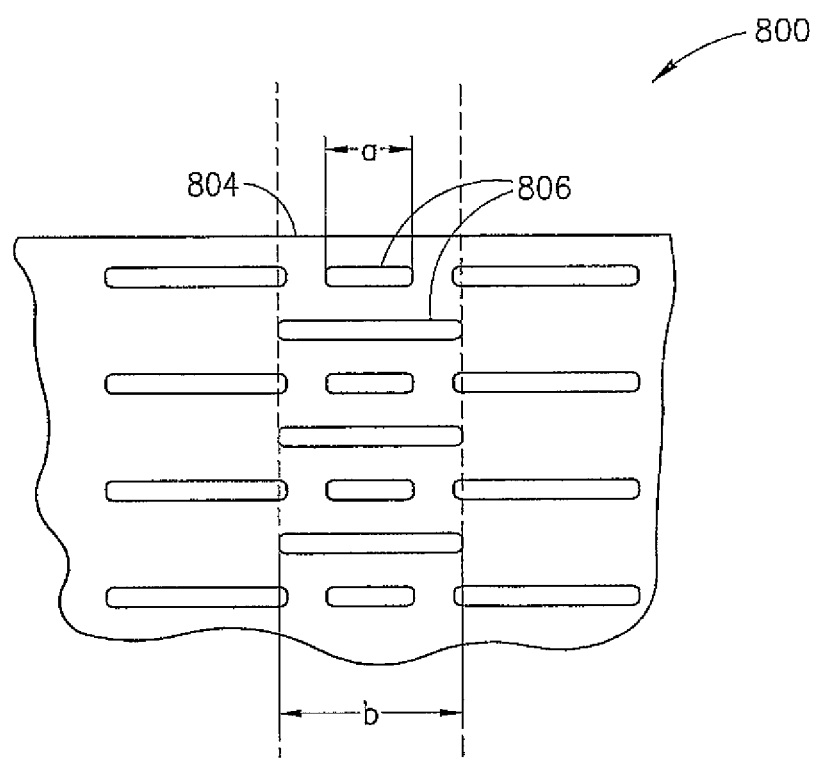
FIG. 8A is a portion of a plan layout of a section of a flow reducing implant with selective narrowing control, in accordance with an exemplary embodiment of the invention.

FIG. 8A is a portion of a plan layout of a section of a flow reducing implant 800 with selective narrowing control, in accordance with an exemplary embodiment of the invention. Flow-reducing implant 800 includes a narrowed section 804. However, section 804 is also expandable, for example, having a plurality of thin slits 806 defined therein. This allows the minimum diameter of flow-reducing implant 800 to be increased after deployment.

In an exemplary embodiment of the invention, section 804 is stiffer than the rest of flow-reducing implant 800, so that pressure suitable for expanding flow-reducing implant 800 will not expand section 804. Alternatively, flow-reducing implant 800 is a self-deploying implant and section 804 is plastically deformed using a balloon. Thus, a delivery system used for flow-reducing implant 800 may include both a restraining element and a balloon element. In case the implantation of a flow-reducing implant fails, extreme expansion of section 804 will substantially negate the function of flow-reducing implant 800 and may allow a new flow-reducing implant to be implanted within or through flow-reducing implant 800, at a later time.

Alternatively, as shown, two sizes of slits 806 are provided, with the degree of resistance to defamation being determined by the sizes and/or relative sizes of the slits.

Figure 8B:
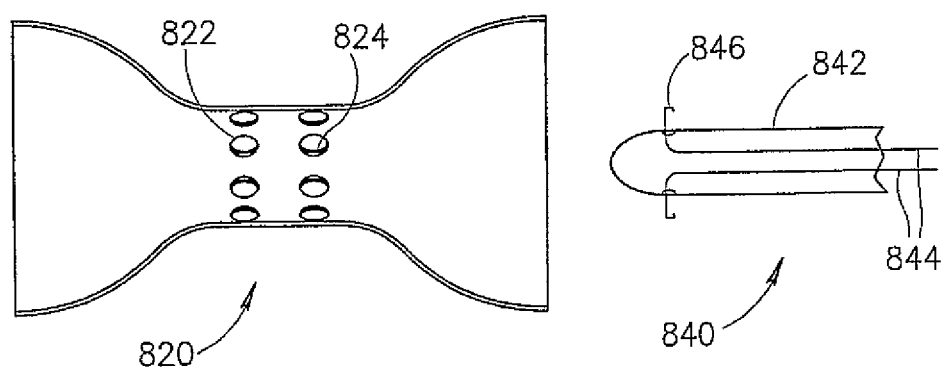
FIG. 8B is a side cross-sectional view of a flow reducing implant and a matching catheter for reducing a diameter of the flow reducing implant, in accordance with an exemplary embodiment of the invention.

FIG. 8B is a side cross-sectional view of a flow reducing implant 820 and a matching reducing catheter 840, which can be used to reduce the narrowing of implant 820, in accordance with an exemplary embodiment of the invention. Flow-reducing implant 820 can be formed generally like flow-reducing implant 800, in that its narrowed section has a selectable diameter. Flow-reducing implant 820 includes a plurality of engagement points 822 that are adapted to be engaged by a plurality of engagers 846 of a catheter 840. Various designs of engagers and engagement points may be used. In the example shown, engagement points 822 include a protruding arc 824 that is engaged by a barbed tip at engager 846. In an exemplary embodiment of the invention, catheter 840 includes a body having a diameter similar to (or smaller, e.g., to allow for spring-back) the desired final diameter of flow-reducing implant 840. When engagers 846 are inserted adjacent to engagement points 822 and catheter 840 is rotated, the barbs engage the arcs. One or more wires 844 are retracted, retracting engagers 846 and arcs 824 towards catheter body 842. In an exemplary embodiment of the invention, body 842 distorts barbs 846 so that they release arcs 824 so that catheter 840 can be removed. Alternatively, other engagement/release mechanisms can be used, for example, barbs that match apertures in flow-reducing implant 820 or provision of grasping heads (e.g., pliers) at engagers 846. Optionally, the narrowing procedure is performed under medical imaging, for example, fluoroscopy.

In an alternative embodiment of the invention, engagement means such as barbs 846 are used to remove the entire flow-reducing implant, optionally for replacement with a different flow-reducing implant and/or re-deployment of the same flow-reducing implant using a balloon on catheter 840 or after removal from the body.

Alternatively or additionally, the flow-reducing implant is removed in the following manner. Flow-reducing implant 820 is a shape memory flow-reducing implant that expands when subjected to body temperature. A balloon having cool fluid circulating there through is brought into flow-reducing implant 820 to cause flow-reducing implant 820 to shrink back to an unexpanded configuration and/or be more amenable for removal.

In some cases however, the decision to remove and/or change a diameter may be made only after a time period, during which vascular tissue may have grown into and attached onto flow-reducing implant 820.

Figure 8C:
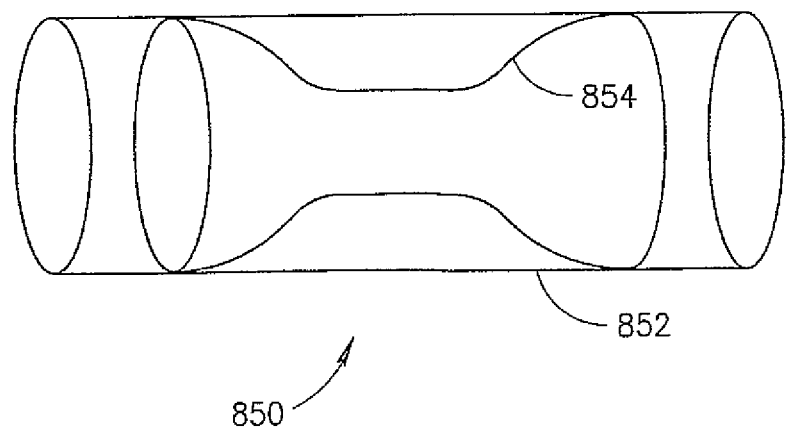
FIG. 8C is a two-part flow reducing implant, in accordance with an exemplary embodiment of the invention.

FIG. 8C is a two-part flow reducing implant 850 including a tubular section 852 and a reducing section 854, in accordance with an exemplary embodiment of the invention, Reducing section 854 may be manufactured to match tubular section 852 or it may be a flow-reducing implant design as described herein or a flare, for example. In either case, tubular section 852 is optionally used to isolate reducing section 854 from the enclosing vascular tissue, thus allowing easier manipulation and/or replacement of section 854. Alternatively or additionally, for example in the coronary sinus, the use of tubular section 852 may be desirable for prevention of damage to the vascular tissue. Alternatively or additionally, tubular section 852 is provided for other reasons, for example, to provide support for axial fixation of reducing section 854 and/or to reduce damage to a surrounding blood vessel. Depending on the embodiment, tubular section 852 and reducing section 854 may be of similar sizes or tubular section 852 may be considerably longer, for example, 25%, 50%, 100%, 200%, 400% or any smaller, intermediate or greater size ratio. The two sections may be inserted at the same time or at different procedures. The two sections may be inserted using a same delivery system or, for example, using two separate delivery systems. Tubular section 852 may be of various designs, for example, be a coil or mesh stent, a stent graft, a graft with stents (or other attachment means) at its ends and/or a plain graft. Tubular section 852 and/or the tips of a flow-reducing implant may be made flexible and/or elastic to adapt to changes in blood vessel diameter.

Figure 8D:
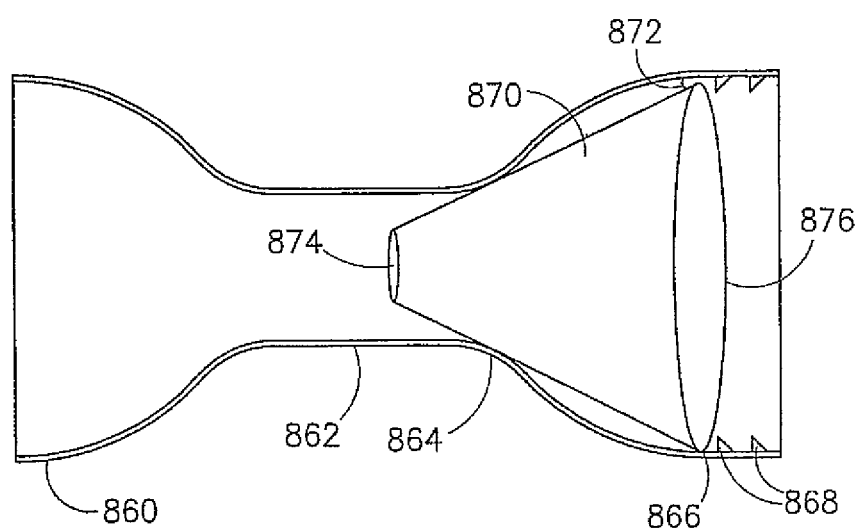
FIG. 8D is a flow reducing implant and insert, in accordance with an exemplary embodiment of the invention.

FIG. 8D is a flow reducing implant 860 including a narrowing insert to reduce the diameter of implant 860, in accordance with an exemplary embodiment of the invention. Insert 870 has its expansion inside flow-reducing implant 860 limited by a narrowed diameter section 862 of flow-reducing implant 860. In an exemplary embodiment of the invention, insert 870 has a funnel shape, with a narrow diameter opening 874 and a larger diameter opening 876. Insert 870 may be formed, for example, from a mesh and may be plastically, elastically, super-elastically and/or shape-memory deformed. In an exemplary embodiment of the invention, the final geometry of insert 870 is defined by its resting points against flow-reducing implant 860. This resting points comprise, for example, a point 864 generally between the narrow and flared sections of flow-reducing implant 860 and a resting point 866 on the flared section of flow-reducing implant 860. In an exemplary embodiment of the invention, a ratchet mechanism is provided to anchor insert 870 in place. Optionally, opening 874 is narrowed further (if required), by advancing opening 876 towards narrowed section 862 of flow-reducing implant 860. Alternatively or additionally, overcoming the ratchet mechanism and retracting opening 876 from section 862 enlarges opening 874. In an exemplary embodiment of the invention, the ratchet mechanism comprises a plurality of inclined barbs or anchors 868, on flow-reducing implant 860. Alternatively or additionally, the ratchet mechanism and/or locking mechanism comprises a barb 872 on insert 870. These ratchets may be overcome, for example, by reducing the size of opening 876 and/or by applying considerable force against the ratchet direction.

Alternatively or additionally to the above described methods of narrowing an implanted flow-reducing implant, in an exemplary embodiment of the invention, a band or clip is applied to the outside of the enclosing blood vessel, urging flow-reducing implant 820 (e.g., at its narrow and/or broad sections) to close. Alternatively, the band is applied alone, without a flow-reducing implant. Exemplary bands and other implants are described in FIG. 6A-6G. Such implants may be used to plastically urge flow-reducing implant 820 closed, in which case, a pliers (optionally adapted to pass through a keyhole) may be used instead of a permanent clamp. The jaws of the pliers are optionally formed to have a cross-section matching desired cross-section of flow-reducing implant 820.

Alternatively, flow-reducing implant 820 is elastic or super-elastic, and a permanent implant is implanted outside the blood vessel. In an exemplary embodiment of the invention, the band or pliers is applied over a wide area, for example, 30%, 50%, 80% or any greater intermediate or smaller percentage of the length of flow-reducing implant 820, to reduce damage to the blood vessel. Alternatively or additionally, the narrowing effect is applied to a weakened part of flow-reducing implant 820, for example, a broad section thereof.

In some locations, for example in larger arteries exhibiting large flow volume and/or blood pressure, flow of blood through slits 1125 (FIG. 7B) may add to turbulence of blood flowing through flow-reducing implant 1100. Such turbulence may contribute to the formation of blood clots that cause embolitic sequella, for example a stroke, at distant locations in the body. While using a single implant with walls that do not have slits may alleviate this problem, flow-reducing implants with non slit walls may not exhibit appropriate expansion capabilities and/or facilitate in situ revision of its configuration.

Figure 8E:
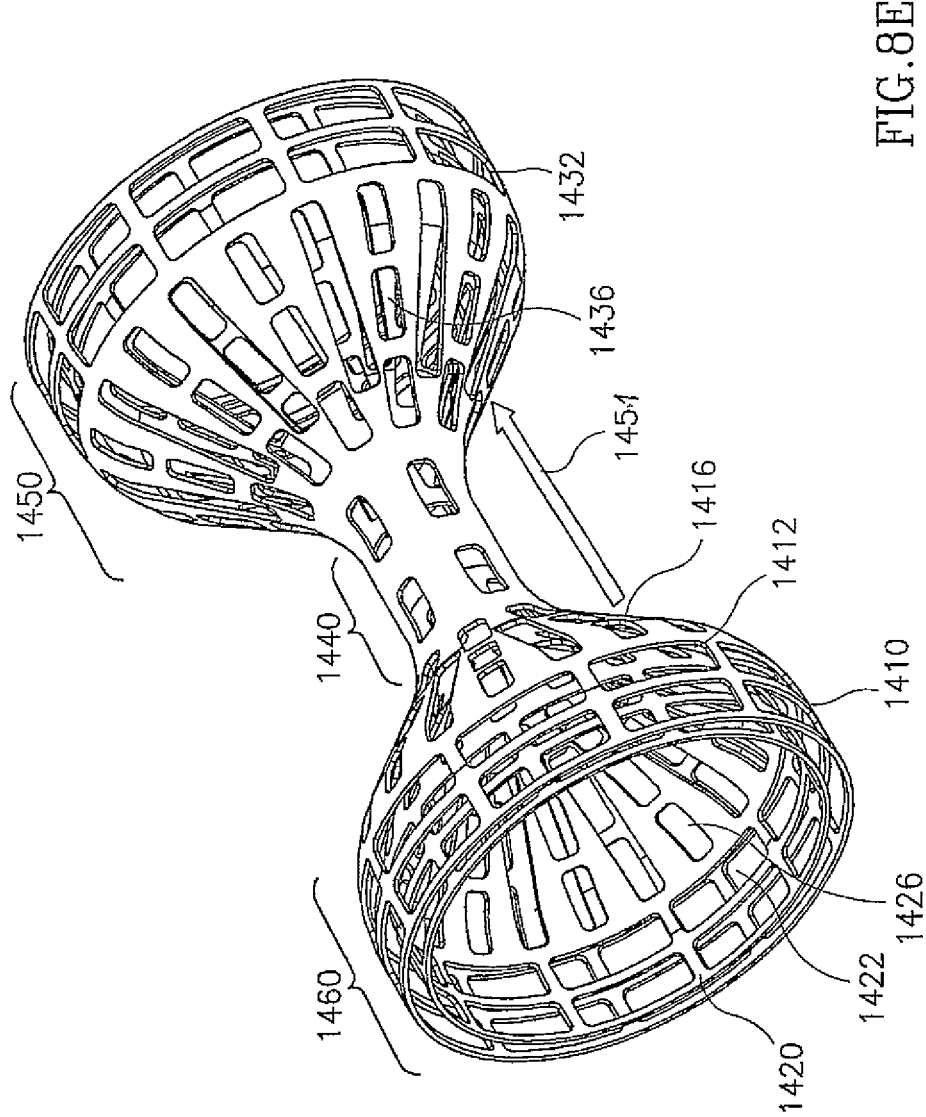
FIG. 8E is an isometric view of a dual layer flow reducing implant, in accordance with an exemplary embodiment of the invention.

FIG. 8E is an isometric view of a dual layer flow-reducing implant 1400 in accordance with an exemplary embodiment of the invention. In an exemplary embodiment, dual layer flow-reducing implant 1400 comprises a first flared section 1450 and/or a second flared section 1460. For purposes of clarity, the components of flare 1460, alone, will be focused on, though similar features can be applied to flared section 1450.

In an exemplary embodiment, dual layer flow-reducing implant 1400 comprises a flared section 1460 comprising an external cone 1420 and an internal cone 1410. Internal cone 1420, for example, comprises slits 1422 and 1426 and external cone 1410 comprises slits 1412 and 1416 so that cones 1410 and 1420 can be transported to an implantation site in a non-expanded state and expanded at the implantation site.

Further expansion of cone 1410 and/or 1420 may be desirable and can be incorporated into their respective designs so that cone 1410 and/or 1420 expand to a first diameter when pressed radially outward by a balloon catheter at a first expansion pressure. Cone 1410 and/or 1420 can then expand to a second, greater, diameter when pressed radially outward by a balloon catheter at a second, greater, expansion pressure.

In an exemplary embodiment, when slits 1422 and 1426 are aligned with slits 1412 and 1416 respectively, blood flows in a direction 1451 (e.g., in a space 132 shown in FIG. 1) and through slits 1432 and 1436. With alignment of slits 1412 with 1422 and/or slits 1416 with 1426, flow-reducing implant 1400 may be implanted into a vessel with a relatively slow flow speed and/or low pressure. For example, with implantation in the coronary sinus narrow area 1440 may fill with tissue that aids in anchoring implant 1400 without risk of an embolism.

Alternatively or additionally, as there is limited or cessation of flow into space 132, a clot forms in area 1440 and stabilizes in its position. Stabilized clot in area 1440 becomes incorporated into the surrounding tissue and against dual cone flow-reducing implant 1400 so that it is further stabilized in its position.

In an exemplary embodiment, slits 1422 and 1426 can be rotated, prior to implantation, in relation to slits 1412 and 1416 so that blood flow in direction 1451 is substantially stopped to various degrees. With misalignment of slits 1422 and 1426, reducing implant 1400 may be implanted into a vessel with a relatively higher flow speed and/or higher pressure, for example a main trunk of an artery thereby protecting the patient against the dangers of embolism migration.

The alignment of slits 1422 and 1426 is optionally set prior to implantation in a blood vessel in relation to slits 1412 and 1416, in order to establish a pre-defined blood flow pattern, and the two layers expanded or allowed to expand, together. To ensure that cones 1410 and 1420 remain fixed in position in relation to each other, cones 1410 and/or 1420 have, for example, a friction surface interface and/or interdigitation. Alternatively or additionally, the two layers may be deployed in different ways, for example, the inner layer may be plastically deployed and the outer layer self-deployed. Possibly, the profile of the two layers does not match along its entire length. Alternatively or additionally, the outer layer is plastically deformed by a self-deploying inner layer (which self deployment may also provide the friction for locking). Alternatively or additionally, cone 1420 may be rotated, for example using a suitable internal engaging catheter, after implantation The flared sections 1450 and 1460 need not be symmetric. For example, the implant may also selecting between flow blockage at one section, the other and optionally both. Flow only into space 132, may assist in clot formation. Flow only out of space 132 may assist in collapsing a surrounding blood vessel, FIGS. 9A-9G illustrate various flow-reducing implant variations, in accordance with exemplary embodiments of the invention. While a sigmoid-like flare is shown, a linear or other flared design may also be provided.

Figure 9A:
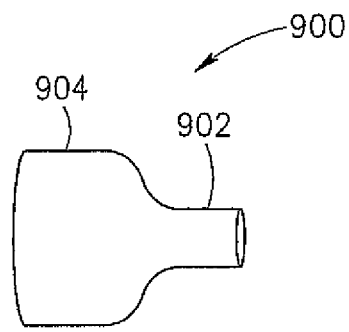

FIG. 9A is a flow-reducing implant 900 with having a narrowed section 902 and a single flared section 904. Narrowed section 902 may point upstream or down stream. One potential advantage of this design is that the delivery system is less likely to get caught inside narrowed section 902. Another potential advantage is that a completely obstructing implant can be provided. In an exemplary embodiment of the invention, however, even such a completely obstructing implant has smooth sides, to prevent damage to the coronary sinus. Possibly, the outer diameter of the completely obstructing implant or a nearly complete flow-reducing implant is increased beyond that of the coronary sinus, to prevent dislodgment of the implant. Alternatively or additionally, one or more barbs on the outside of the implant may be provided. Optionally, a cone shaped flow-reducing implant is provided with one or more openings for blood flow on the face of the cone, rather than at its apex as shown.

Alternately to a plain flow-reducing implant, the narrowing may be a valve, for example, a valve that opens, to a full or partial diameter, after a suitable pressure is achieved in the coronary sinus distal from the right atrium. For example, a leaflet valve or other type of vascular valve as known in the heart may be provided.

Figure 9B:
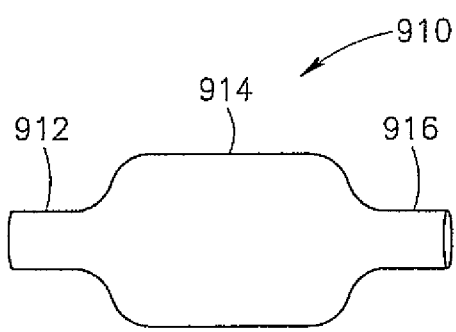

FIG. 9B shows an alternative flow-reducing implant 910; with two narrowed sections 912 and 916 sandwiching a flared section 914 between them, in accordance with an exemplary embodiment of the invention. Optionally, the different narrowed sections have a different inner diameter. Optionally, the narrowed sections are selectively expanded using a balloon to achieve a desired pressure profile.

Figure 9C:
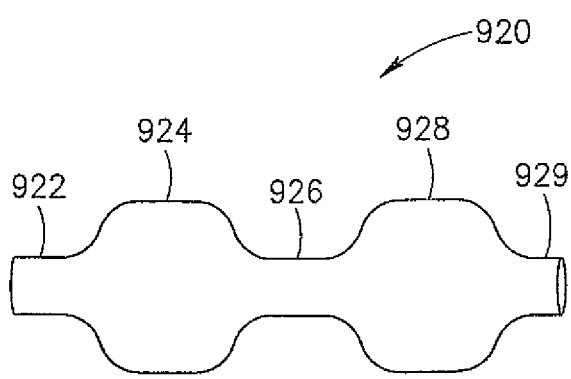

FIG. 9C is an alternative flow-reducing implant 920 with three narrowed sections 922, 926 and 929 and two flared sections 924 and 928 between the narrowed sections, in accordance with an exemplary embodiment of the invention.

Certain blood vessels may exhibit a taper along their length, for example forming an angle 1310, shown in FIG. 9D. Vessels that change in size along their length may occur, for example, in the coronary sinus as it joins into the right atrium. In a tapered blood vessel it may be desirable to utilize a tapered-type flow-reducing implant 930 (FIG. 9E), seen in detail in FIG. 9D, in accordance with exemplary embodiments of the invention.

FIG. 9D is an isometric view of an exemplary embodiment of a tapered flow-reducing implant 1300, (with a similar configuration to implant 930) in accordance with an exemplary embodiment of the invention. Tapered flow-reducing implant comprises a smaller flared section 1330, a narrowed section 1340 and larger flared section 1320. The size of smaller flared section 1330, for example, is governed one or more slits 1342 that are transverse to the axis of narrowed section 1340 and one or more slits 1346 that are longitudinal to the axis of narrowed section 1340.

The size of larger section 1320 is governed, for example, by two or more slits 1322 that are transverse to the axis of narrowed section 1340 and/or two or more slits 1320 that are longitudinal to the axis of narrowed section 1340.

Optionally, slits 1342, 1346, 1322 and/or 1326, be varied size and/or configuration to govern the shape of flared sections 1320 and/or 1330. Alternatively or additionally, slits 1342, 1346, 1322 and/or 1326 may be have various arrangements to provide different contours to flared sections 1320 and/or 1330 and/or narrowed section 1340.

While openings 1330 and 1320 are shown as being round, they may have a variety of configurations to conform to different vessel configurations as noted above. Further, the ratio between opening 1330 and 1320 may be varied to conform to any vessel diameter where flow-reducing implant 1300 is implanted. As in other figures, the material of the implant is shown distorted, while in some embodiments, it may be the slits, possibly in addition to the material, which is distorted.

Figure 9E:
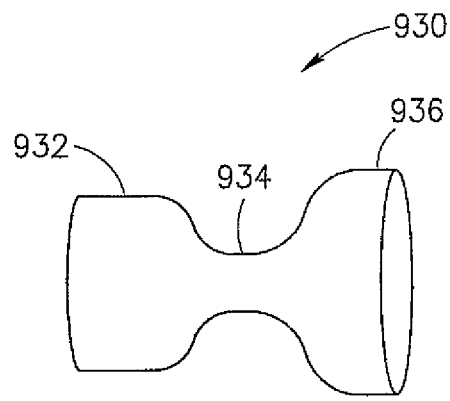

FIG. 9E is a tapered flow-reducing implant 930 in which one flared section 932 has a smaller diameter than a second flared section 936, but larger than an intermediate narrowed section 934, in accordance with an exemplary embodiment of the invention.

Figure 9F:
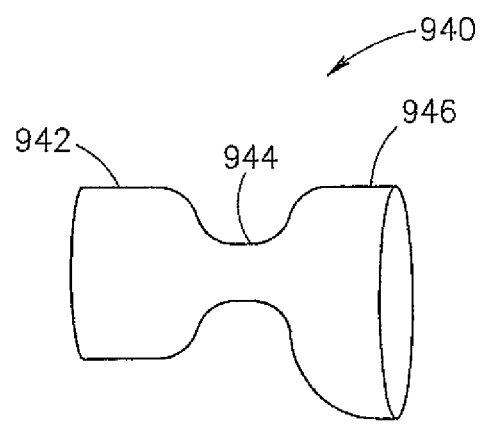

In FIG. 9F is a flow-reducing implant 940 that is not axially and/or rotationally symmetric around its axis, in accordance with an exemplary embodiment of the invention. In an exemplary embodiment, a first flared section 946 is distorted relative to an axis defined by a second flared section 942 and a narrowed section 944.

Optionally, flow-reducing implant 940 is curved. In an exemplary embodiment of the invention, asymmetric or curved flow-reducing implants include special markings, for example, radio-opaque or radio-transparent areas, to assist correct orientation of flow-reducing implant 940 in a blood vessel.

Figure 9G:
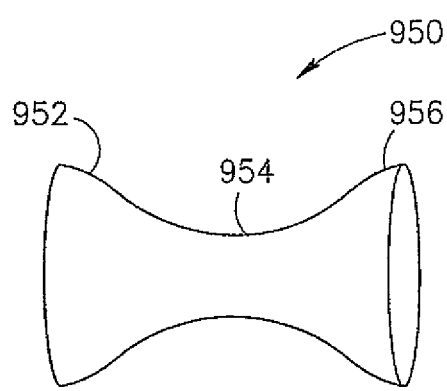

FIG. 9G is a flow-reducing implant 950, in which a narrowed section 954 is a sleeve 954, in accordance with an exemplary embodiment of the invention. Sleeve 954, for example, is formed of a flexible graft material, such as Dacron or GoreTex. Flow-reducing implant 950 further comprises at least one of two outer rings 952 and 956 that serve to anchor flow-reducing implant 950 in the blood vessel. A potential advantage of using a sleeve is that it can bend to conform to the vein geometry and/or dynamics. Other flow-reducing implant designs can also bend. Optionally, the graft material is elastic, so it can serve as a pressure limiting valve, to better control coronary sinus pressure. Optionally, a constraining ring is provided on the outside of section 954, to restrict the lumen of flow-reducing implant 950. Optionally, the ring is placed on flow-reducing implant 950 during the procedure, to achieve a desired narrowing effect. Alternatively or additionally, the ring is expandable, for example using a balloon, to allow controlling the narrowed section of flow-reducing implant 950. Optionally, the ring is sutured to narrowed section 954. Optionally, section 954 is stiffened, for example, using a wire, as known in the art of stent-grafts.

In an exemplary embodiment of the invention, flow-reducing implant 100 is provided in kit form, possibly with a delivery system, a flow-reducing implant diameter control system, additional flow-reducing implants, external bands and/or other means for reducing its inner diameter, and including instructions for use and/or size markings. Optionally, flow-reducing implant 940 is provided inserted into a delivery system or packaged with a delivery system.

As noted above, in some embodiments of the invention a flow reducing implant is constrained by providing a band on the outside of the implant.

FIGS. 10A-10B are an isometric view and detail, respectively, of a ringed mesh-type flow reducing implant embodiment, in accordance with an exemplary embodiment of the invention. In an exemplary embodiment, mesh-type flow-reducing implant 1500 (FIG. 10A) comprises a flare shoulder 1502 and/or a flare shoulder 1504 that are relatively long in length, for example, to increase the area of contact between flow-reducing implant 1500 and surrounding vessel walls. Alternatively or additionally, tissue may grow through the mesh of flare shoulders 1502 and/or 1504, providing good anchorage of mesh-type flow-reducing implant 1500. Optionally, mesh-type flow-reducing implant 1500 comprises and/or is coated with materials that promote tissue ingrowth. A rim 1620, which may be, for example jagged or smooth is also optionally provided on each shoulder.

Optionally, the initial shape of mesh-type flow-reducing implant 1500 is governed by one or more bands 1522 and/or 1524 that constrict an area 1528 of mesh-type flow-reducing implant 1500. In an exemplary embodiment, the surrounding tissue collapses onto mesh-type flow-reducing implant 1500 to reduce blood flow through the walls of constriction area 1528. While two bands 1522 and 1524 are shown, a single band, for example band 1522 alone, may be used to create constriction area 1528.

In an exemplary embodiment, an operator manually tying their ends together, prior to implantation, adjusts the rings formed by band 1522 and/or 1524 in circumference, for example. Adjustment of band 1522 and/or 1524 prior to implantation allows the operator to establish constriction area 1528 with a specific size to reduce blood flow and thereby promote angiogenesis. Alternatively or additionally, a balloon catheter, for example, is expanded in area 1562 to cause expansion of bands 1522 and/or 1524, thereby expanding area 1562 to increase blood flow there through. In this fashion, blood reduction through flow-reducing implant 1500 can be regulated prior to placement and/or following placement of flow-reducing implant 1500 in a blood vessel.

In an exemplary embodiment, band 1524 rips when a large expansion force is placed against it. To adjust the diameter of area 1528 following implantation, a balloon catheter is positioned inside area 1562 and expanded until the pressure exceeds that which is required to rip band 1524. With band 1524 ripped, the area of mesh area 1562 directly under it expands so that area 1562 expands in diameter so that it has the diameter of ring 1522.

Optionally, band 1524 has a smaller diameter than band 1522, providing two levels of expansion. For example, so that as a balloon catheter is expanded to a first diameter, it expands smaller diameter band 1524, increasing the diameter of constriction area 1528 to a first expanded diameter. Should further increase in flow be desired, a balloon catheter is expanded to a second diameter and expands larger diameter band 1524 and/or smaller diameter band 1524, increasing the diameter of constriction area 1528 to a second expanded diameter.

Ring 1524 has, for example, a diameter of 6 millimeters while ring 1522 has a diameter of 8 millimeters so that area 1562 has flow passage of 6 millimeters. By expanding an expansion balloon inside area 1562 and causing ring 1524 to rip, the area under ring 1524 expands. However, ring 1522, with its diameter of 8 millimeters, maintains its integrity. Hence area 1562 now has a flow passage of 8 millimeters (less the thickness of the mesh or other material from which the implant is formed.

FIG. 10B is a detail of an embodiment of ring 1522 comprising an adjustable band 1540 that forms ring 1522 and is held at a specific diameter by a clasp 1544. Alternatively or additionally, adjustable band 1540 is maintained at a specific diameter by a clasp 1546. In an exemplary embodiment, clasps 1544 and/or 1546 hold adjustable band 1540 so that during implantation, ring 1522 remains at a specific diameter until, for example, an expanding balloon catheter is expanded against adjustable band 1540 and the diameter of ring 1522 is expanded. In an exemplary embodiment, clips 1544 and 1546 comprise, for example, a nylon material that holds band 1522 at a specific diameter and allow expansion of the diameter only under expansion pressure from, for example, a balloon catheter. Optionally, two clasps are provided, so no part of band 1540 sticks out from the ring. In an exemplary embodiment of the invention, the clasps are "C" shaped and band 1540 optionally include bumps that prevent sliding of the band through the clasps. Alternatively or additionally, friction prevents such sliding.

In an exemplary embodiment, flare shoulders 1504 and/or 1502 are 0.5 centimeters to 1 centimeter in length through they could be less than 0.5 centimeters or greater than 1 centimeter in length, for example, depending upon vessel configuration.

In an exemplary embodiment, mesh-type flow-reducing implant 1500 comprises strands that form its mesh comprising gortex, Dacron and/or steel. Further, the material comprising the mesh can be configured to be flexible or rigid, depending, for example, on the materials, its thickness, based upon, for example the flow dynamic dynamics desired.

Figure 11:
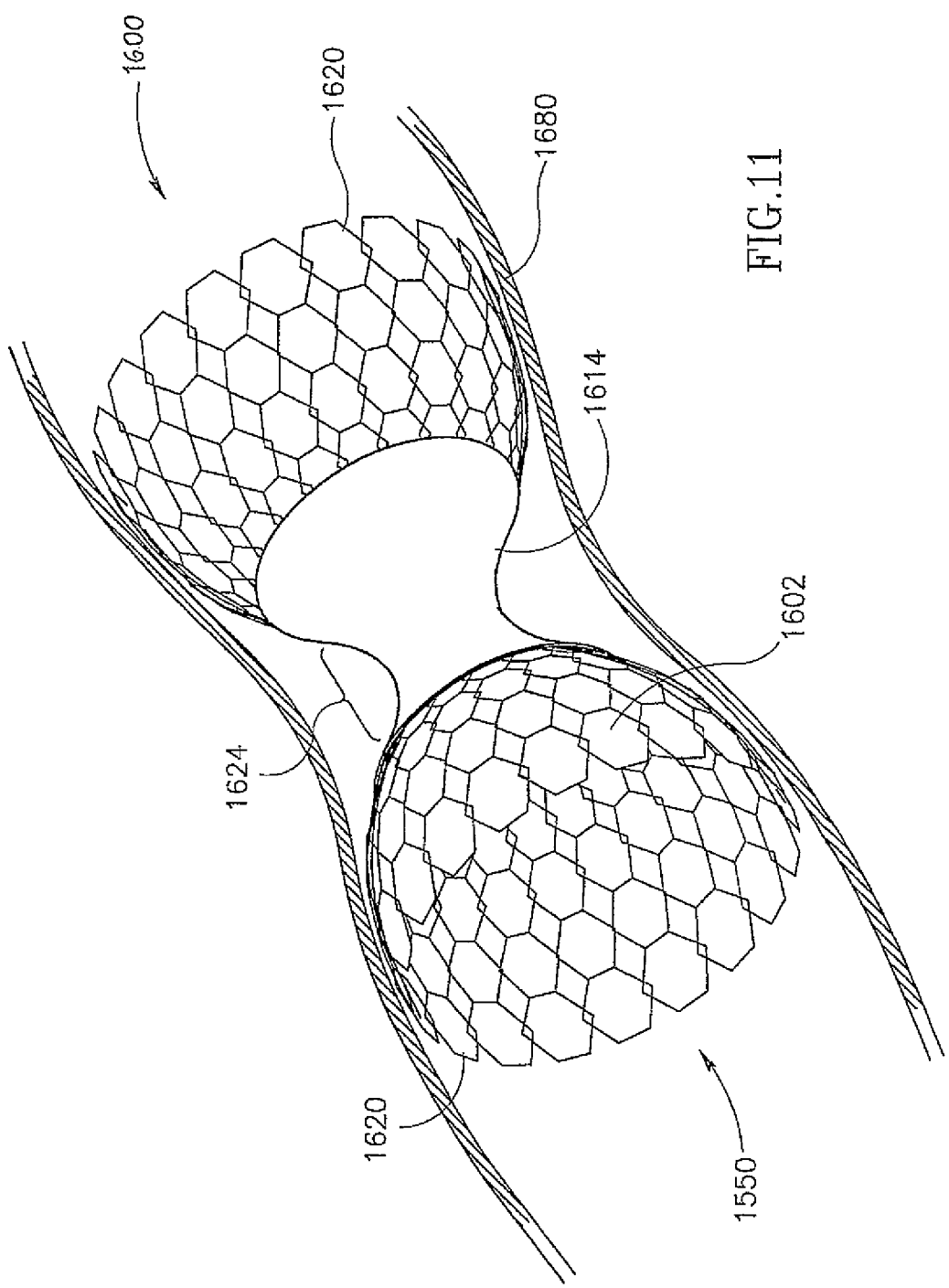
FIG. 11 is an isometric view of a partially covered mesh-type flow reducing implant embodiment, in accordance with an exemplary embodiment of the invention.

FIG. 11 is an isometric view of a partially covered mesh-type flow reducing implant embodiment 1600, in accordance with an exemplary embodiment of the invention. Mesh-type flow reducing implant 1600 comprises a covering 1614 over or inside narrow section 1624, implanted in a blood vessel 1680, shown in cross section. In an exemplary embodiment, mesh-type flow reducing implant 1600 comprises one or more flare shoulders 1602 that contact blood vessel 1680 to provide anchoring. A rim 1620, which may be, for example jagged or smooth is also optionally provided on each shoulder.

Alternatively or additionally, mesh-type flow reducing implant 1600 comprises a covering 1614 the restricts blood flow through the surface of flow reducing implant 1600 and/or blood turbulence in an area of constriction 1624, thereby reducing danger of embolitic migration problems.

In an exemplary embodiment of the invention, covering 1614 comprises a separate, flexible layer, that is attached to flow reducing implant 1600 at several points (e.g., at constriction area 1624 and/or flare shoulders 1602) to prevent tearing when implant 1600 expands. Prior to expansion, for example, covering 1614 is folded and/or pleated. Alternatively or additionally, covering 1614 has a low bulk and, for example, is integrated into flow reducing implant 1600 structure, for example, so that it substantially spans the open areas of the mesh. Examples of materials comprising covering 1614, include gortex, latex and/or silicone, on the inside and/or outside of flow reducing implant 1600.

Figure 12:
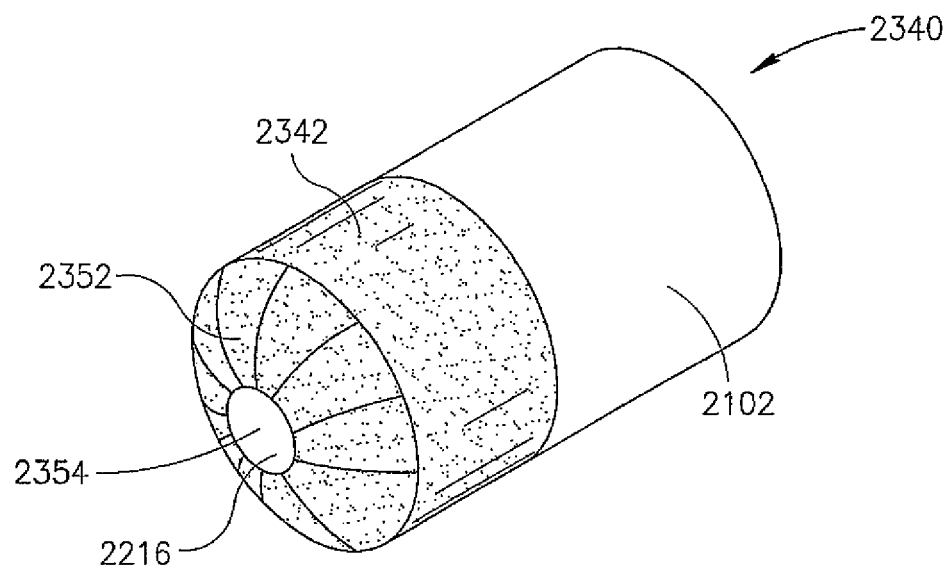
FIG. 12 is an isometric view of a sheath-type flow reducing implant, in accordance with an exemplary embodiment of the invention.

FIG. 12 is an isometric view of a sheath-type flow reducing implant 2340, in accordance with an exemplary embodiment of the invention. Sheath-type flow reducing implant 2340 comprises a sheath 2342 that encircles at least a portion of outer wall 102. Sheath-type flow reducing implant 2340 with a single sheath 2342 differs from implant 950 (shown FIG. 9G) in which a narrowed section 954 is shown with two flared sides and supported by stents or rings 952 and/or 956. Connected to sheath 2342 and/or an extension thereof is a sheath projection 2352, with an opening 2354 to allow passage of blood flow via lumen 2216. Sheath projection 2352, for example, can be configured with grooves and/or projections to further control the amount of obstruction of the central blood flow stream. In an exemplary embodiment of the invention, sheath 2352 includes a stiffener ring which maintains its opening patent. Alternatively or additionally, one or more stiffening axial or radial struts are provided to assist in maintaining the shape of sheath 2352.

Figure 13:
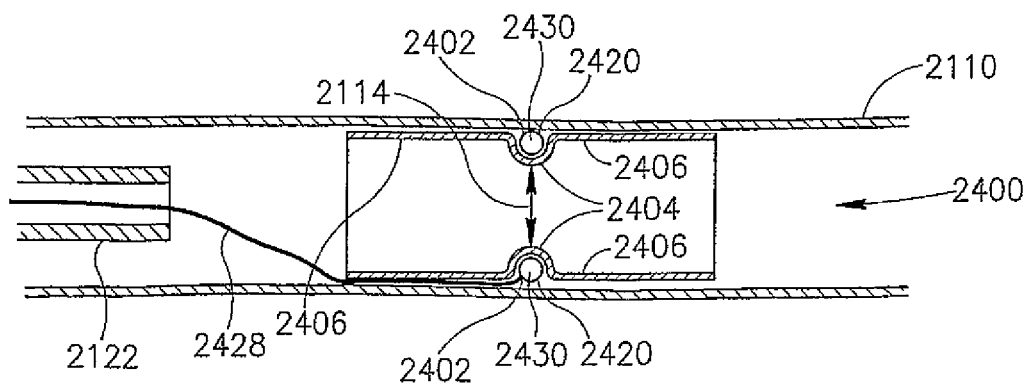
FIG. 13 is longitudinal section of an inflatable tube-type flow reducing implant, in accordance with an exemplary embodiment of the invention.

FIG. 13 is longitudinal section of an inflatable tube-type flow reducing implant 2400, in accordance with an exemplary embodiment of the invention. Inflatable tube-type flow reducing implant 2400 comprises a long wall 2406, a portion of which is surrounded by a ring-shaped tube 2420. Optionally, tube 2420 can be located along any portion of long wall 2406 and/or of any configuration that reduces blood flow through lumen 2114. In an exemplary embodiment of the invention, tube 2420 replaces the function of ring 1522 of FIG. 10A.

In an exemplary embodiment, tube 2420 has an interior space 2430 enclosed within a circular wall 2402 that is, for example, inflatable using a hose 2428. In an exemplary embodiment, tube 2420 inflates so that interior 2430 has two or more cross sectional diameters, thereby allowing adjustment of narrow lumen 2114 to modify the amount of reduction in blood flow. Hose 2428 is optionally removed or torn off after deployment. Alternatively or additionally, hose 2428 may be attached after deployment, for example having a needle tip used to inject fluid into tube 2420. Alternatively or additionally, tube 2420 may be torn or punctured after implantation, to increase the diameter of the narrowing.

Alternatively or additionally, tube interior 2430 contains a material that absorbs liquid, thereby expanding. Following implantation, for example, tube 2420 absorbs liquid and interior 2430 increases in size until tube 2420 reaches its expanded state.

Alternatively or additionally, wall 2402 and/or tube 2430 comprise a resilient material, for example Nitinol, and expand to a final state without inflation. Alternatively or additionally, flow-reducing implant 2400, and/or embodiments mentioned below, are manufactured from a biocompatible material, comprising, for example, a soft silicone elastomer and/or another soft material such as latex, Teflon, gortex, Kevlar and/or polyurethane.

Alternatively or additionally, interior 2430 is filled, for example with a spongy material, for example that is different from the material comprising long wall 2406 and/or wall 2402. Spongy material of interior 2430, for example, remains compressed in a compact size until its exit from catheter 2122 whereupon interior 2430 expands, causing the expansion of tube 2420.

In an exemplary embodiment, long wall 2406 is contoured and comprises a shape memory material and achieves its final state, including a bulge 2404, upon exit from catheter 2122. Alternatively or additionally, long wall 2406 is, for example, not contoured and tube 2420 presses against long wall 2406 to create bulge 2404.

In an alternative embodiment of the invention, wall itself 2406 comprises a balloon, which is inflated. Alternatively or additionally, wall 2406 is manufactured with a varying thickness, for example being made of a flexible plastic cylinder with its top and bottom reamed out.

Figure 14:
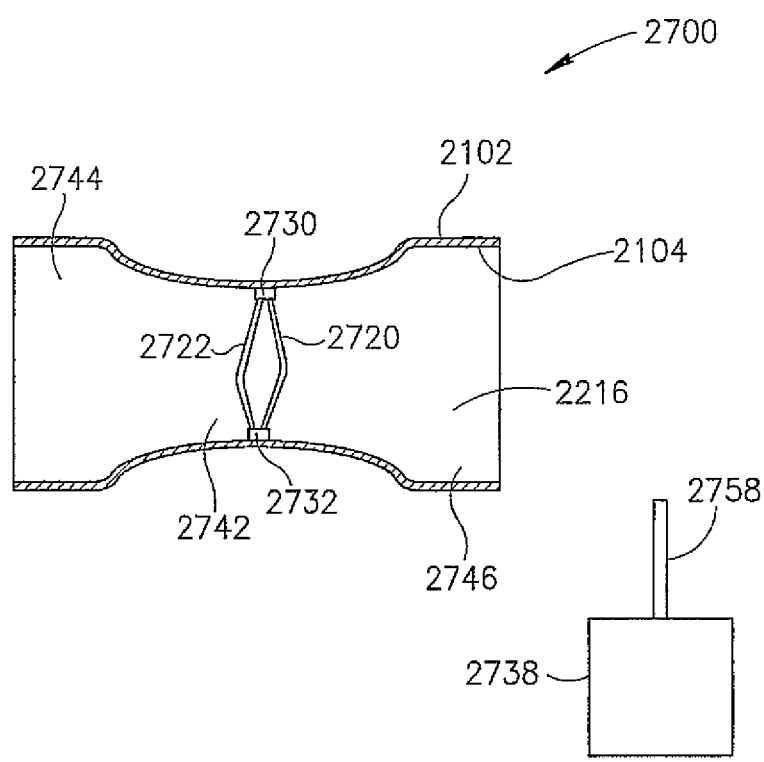
FIG. 14 is a longitudinal section of a flow reducing implant with shape-conforming elements, in accordance with an exemplary embodiment of the invention.

FIG. 14 is a longitudinal section of a flow reducing implant with shape-conforming elements 2700, in accordance with an exemplary embodiment of the invention. Shape-conforming element implant 2700 comprises one or more shape-conforming elements 2720 and/or 2722 that can be remotely induced to change their configuration. Remote control of the configuration of elements 2720 and/or 2722 causes, for example, change in configuration, constriction and/or expansion of narrow lumen 2742, flare 2744 and/or flare 2746 without associated hazards of an invasive procedure. As narrow lumen 2742, flare 2744 and/or flare 2746 change their configuration; the blood flow is obstructed to a greater or lesser extent, thereby promoting angiogenesis.

Shape-conforming elements 2720 and/or 2722, for example, are charged so that as they receive impulses from impulses 2730 and/or 2732, they change into one or more different geometric shapes and/or configurations. The shapes of elements 2720 and/or 2722 induced by impulsers 2730 and 2732 changes the reduction in blood flow, thereby influencing angiogenesis.

For example, one or both shape-conforming elements 2720 and/or 2722 straighten, they exert outward expansion pressure on narrow lumen 2742, thereby allowing blood flow there through to increase. When one or both shape-conforming elements 2720 and/or 2722 bend further than depicted in FIG. 14 they pull the walls of narrow lumen 2742 inward, causing lumen 2742 to narrow, thereby reducing blood flow there through.

Alternatively or additionally, when shape-conforming elements 2720 and/or 2722 bend or straighten wall 2102 along narrow lumen 2742 may change the obstruction of the lumen by wall 2102 to influence angiogenesis.

Alternatively or additionally, shape-conforming elements 2720 and/or 2722 are located exterior to flow-reducing implant 2700, for example along outer wall 2102. Alternatively or additionally, other shape-conforming elements 2720 and/or 2722 may be located along flares 2744 and/or 2746 to provide additional and/or alternative remote control of flow-reducing implant 2700.

Optionally, impulses provided by impulsers 2730 and 2732 to induce changes in shape-conforming elements 2720 and/or 2722 and comprise one or more of: RF, acoustic waves such as ultrasound and/or low frequency sound, heat, electricity, electromagnetic, radiation. Alternatively or additionally, impulsers 2730 and 2732 mediate a chemical reaction that modifies elements 2720 and/or 2722, thereby changing their configuration.

In an exemplary embodiment, a director 2738, external to the patient, directs impulsers 2730 and 2732 to provide impulses to shape-conforming elements 2720 and/or 2722, thereby causing the changes in geometric shape. Director 2738, for example, directs impulsers 2730 and 2732 via radio waves from an antenna 2758. Impulses 2730 may be, for example ratchet mechanisms or motors powered or stimulated by such signals, to shorten bands that surround the implant. In an exemplary embodiment of the invention, impulsers 2730 comprise one or more magnetic motors that include a magnetic gear which is turned by the effect of a rotating magnetic field applied outside the body and which taming causes a tightening of a band (e.g., 2722, 2720).

Alternatively or additionally, elements 2720 and/or 2722 are sensitive to waves that are propagated external to the patient. For example, director 2738 provides one or more of: RF, acoustic waves such as ultrasound and/or low frequency sound, heat, electricity, electromagnetic and radiation to influence the configuration of elements 2720 and/or 2722. Impulsers 2730 and 2732 may then be optional, or be used only to provide a ratchet mechanism.

In an exemplary embodiment, shape-conforming elements 2720 and/or 2722 comprise a material with a positive charge, for example positively charged plastic and/or silicone rubber. Alternatively or additionally, shape-conforming elements 2720 and/or 2722 comprise a negatively charged material.

Optionally, shape-conforming elements 2720 and/or 2722 are manufactured from a material comprising charged lithium ions. In an exemplary embodiment, waves cause the charged lithium ions to align, thereby changing the geometry of shape-conforming elements 2720 and/or 2722 to cause changes in the shape of outer wall 2102 and/or inner wall 2104.

In an exemplary embodiment, the strength and/or length of impulses aid in changing shape-conforming elements 2720 and/or 2722. For example, impulsers 2730 and 2732 provide an electric impulse of between 0.1 volts and 0.5 volts (optionally, 0.1 volts or less or 0.5 volts or more), for a period of 10 msec or longer or 6 msec. or shorter. The factors influencing the impulse chosen, for example, depend upon materials comprising shape-conforming elements 2720 and/or 2722, their responsiveness to the impulses and/or the desired changes in their shapes to influence the shape of flow-reducing implant 2700.

Flow-reducing implant 2700, with shape-conforming elements 2720 and/or 2722 allows modification in shape and/or blood flow reduction following implantation of flow-reducing implant 2700 in coronary sinus 2110 without an invasive procedure. Alternatively or additionally, an embodiment of shape-conforming element implant 2700 that assumes its installed shape without, for example, the use of balloon catheter 1000 may be desirable.

In an alternative embodiment, externally applied RF radiation is received by threads 2722 and 2720, which act as antenna and heat up, thereby expanding. Alternatively or additionally, such heating is used to inflate a balloon band, for example by causing an irreversible chemical reaction that releases gas.

Figure 15:
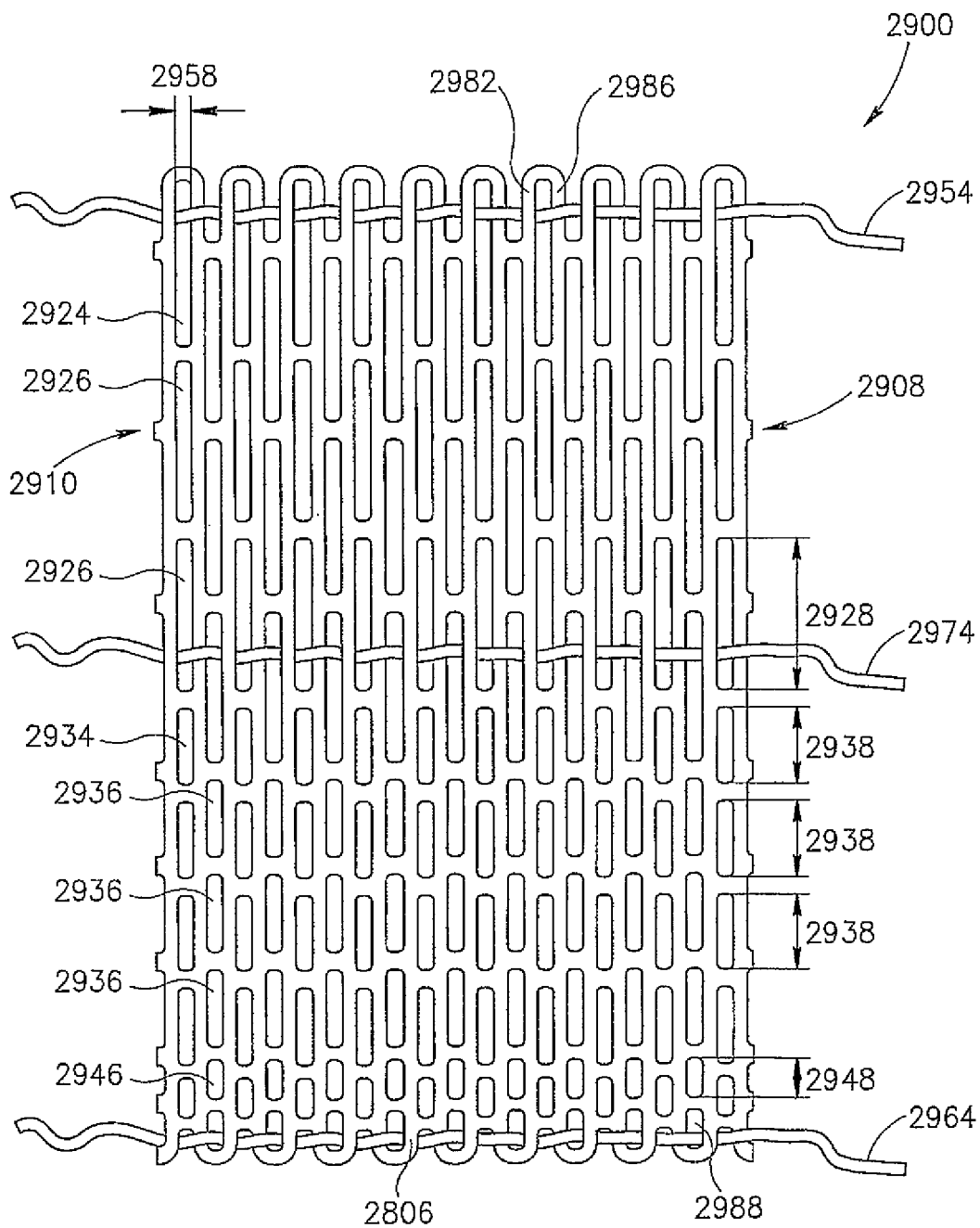
FIG. 15 is a plan layout of a cord-type flow reducing implant, in accordance with an exemplary embodiment of the invention.

FIG. 15 is a plan layout of a cord-type flow reducing implant 2900, in accordance with an exemplary embodiment of the invention. In an exemplary embodiment, cord-type flow-reducing implant 2900, comprises a preformed shape that will easily spring into its installed shape without, for example, use of balloon catheter. Alternatively, a balloon based expansion mechanism is provided. In an exemplary embodiment, one or more edges 2910 are joined to one or more edges 2908 to form cord-type flow-reducing implant into a tubular shape with lumen 806 passing there through.

In its assembled state, cord-type flow-reducing implant 2900 comprises a row of slits 2924 through which a cord 2954 passes, that is modified with minimal expansion pressure from balloon catheter.

In an exemplary embodiment, cord 2954 is woven to pass under a lead post 2982 and over a trailing post 2986 so that cord 2954 is woven across cord-type flow-reducing implant 2900. Alternatively or additionally, cord 2954 is expandable and attached to surfaces of slots 2924, for example their surfaces facing lumen 2806 or their opposite (outside) surfaces. Optionally, the cord blocks blood flow through the wall of the reducer.

In an exemplary embodiment, after cord-type flow-reducing implant 2900 expands to its initial configuration automatically upon exiting a delivery sheath. When further size modification is required, a balloon catheter is introduced into the interior of cord-type flow-reducing implant 2900. The balloon catheter is inflated, for example, between 3-4 atmospheres (optionally, 3 atmospheres or less or 4 atmospheres or more), to cause cord 2954 to expand (or it may be loose) radially outward, thereby allowing slit 2958 to expand further and the diameter of the adjacent flared section to increase.

Alternatively or additionally, at least a portion of an edge 2910 is detached from at least a portion of an edge and at least a portion edge 2910 and edge 2908 overlap. When expansion is required, expansion force is applied, for example, between 7-8 atmospheres (optionally, 7 atmospheres or less or 8 atmospheres or more) is applied. Cord 2954, in response to the pressure, elongates (or is loose and tightens) so that edge 2910 draws closer and/or passes edge 2908, allowing cord-type flow-reducing implant 2900 to attain another, expanded, diameter.

In an exemplary embodiment, cord 2954 comprises a plastic material that stretches to two or more lengths, depending upon the expansion pressure that is applied to it. Hence, at a lower pressure, cord 2954 expands to a first length, thereby defining a first narrow diameter of cord-type flow-reducing implant 2900. Subsequently a second expansion pressure is applied and cord 2954 attains a second, longer, length, thereby defining a second diameter, wider than the narrow diameter.

Alternatively or additionally, cord-type flow-reducing implant 2900 includes one or more diameters in which edge 2910 and edge 2908 are separated by a space, thereby providing an interrupted lumen surface. Alternatively or additionally, cord 2954 severs upon application of, for example, pressure between 9-10 atmospheres (optionally 9 atmospheres or less or 10 atmospheres or more). Upon severing cord 2954, edge 2910, for example, maximally separates from edge 2908; thereby applying unrestricted pressure against coronary sinus 2110.

In an exemplary embodiment, cord 2954 of flow-reducing implant 2900 comprises a biocompatible material that dissolves in the environment of coronary sinus 2110, for example, a material comprising galactic acid and/or polygalactic acid and/or other materials with similar properties. In an exemplary embodiment, flow-reducing implant 2900 is placed in coronary sinus 2110 and the balloon catheter is used to expand it so that its outer surface contacts the inside surface of coronary sinus 2110. Over a period of time, for example cord 2954 degrades, depending upon the biodissolvable material comprising cord 2954. (Optionally, degradation of cord 2954 occurs in less than three days or more than three days, dependent upon its composition and/or desired duty cycle.) Once cord 2954 has dissolved, flow-reducing implant 2900 retains and/or assumes a shape with its outer surface in contact with the inner surface of coronary sinus 2110.

With cord 2954 dissolved, further expansion of inner diameter of flow-reducing implant 2900 is accomplished with balloon 1010 at a low atmospheric pressure due to the fact that edge 2908 passes edge 2910 without the hindrance of cord 2954. Hence, to cause edge 2908 to pass edge 2910, expansion force need only overcome the stiffness of the material comprising flow-reducing implant 2900. In an exemplary embodiment, a pressure of between 3-4 atmospheres (optionally 3 atmospheres or less or 4 atmospheres or more), causes expansion of wall the lumen through flow-reducing implant 2900.

In an exemplary embodiment of the present invention, flow-reducing implant 2900 comprises cord 2954 passing through slits 2924 and a cord 2964 passing through slots 2988. Alternatively or additionally, flow-reducing implant 2900 comprises three or more cords: 2954, 2964 at either end and a cord 2974 passing through slots 2926 substantially in the middle of flow-reducing implant 2900.

Cords 2954, 2964 and/or 2974 serve to maintain the shape and/or appropriate lumen diameter following installation. To expand the lumen through flow-reducing implant 2900, balloon catheter 1000 is used to expand and/or sever cords 2954, 2964 and/or 2974. Alternatively or additionally, sever cords 2954, 2964 and/or 2974 are biodissolvable, dissolving in the environment of coronary sinus 2110.

It should be noted that when implant 2900 is deployed, the final shape is that of a cone, the relative lengths 2948, 2938 and 2928 of the slits 2946, 2936 (and 2934) and 2926, respectively, generally define the geometry of the expanded device. As shown, the cone shape is convex. However, other shapes, for example, concave may be provided instead. Also shown in this embodiment is that the slits are staggered, so that the expansion will be generally distributed over the surface of the implant.

While the above has been described for use in coronary veins, a flow reducing implant with similar design may also be used in other veins, for example, popliteal, tibial or saphenous veins. In an exemplary embodiment of the invention, described in greater detail below, one or more flow reducing implants are implanted in popliteal veins, to increase backpressure and possibly enhance tissue perfusion pressure and/or redistribute blood flow in the leg. It is expected that pooling will not occur due to the existence of alternative drainage paths in the leg. Multiple insertions of flow reducing implants may be used to treat and/or hide varicose veins.

Within the closed facial compartments of the lower limb, a plurality of thin-walled, valved venae comitantes are subjected to intermittent pressure both at rest and during exercise. The pulsation of the adjacent arteries help to move the blood up the limb. Also, the contractions of the large muscles within the compartments during exercise compress these deeply placed veins and force the blood up the limb. The superficial saphenous veins, except near their termination, lie within the superficial fascia and are not subject to these compression forces. The valves in the perforating veins, which interconnect deep and surface veins, prevent the high-pressure venous blood from being forced outward into the low-pressure superficial veins. Moreover, as the muscles within the closed facial compartments relax, venous blood is sucked from the superficial into the deep veins. Lower limb venous pressure increases to dependency, stimulating a local sympathetic axon reflex, which triggers precapillary and arteriolar vasoconstriction. The resulting decrease in arterial calf inflow, known as the venoarterial response (VAR), is impaired in critical ischemia. The median VAR was found to be significantly lower in patients with stable claudication than in normal subjects or patients following successful revascularization (29.1 versus 59.5 and 63.9 percent respectively). Thus, patients with claudication apparently have a significant impairment of orthostatic sympathetic autoregulation. It should be mentioned that neovascularization is considered an important cause of venous reflux recurrences after ligation of foot veins. The pathogenesis of this phenomenon is so far obscure. It has been hypothesized that a hemodynamic factor could be the trigger initiating the process of neovascularization. In an exemplary embodiment of the invention, such a factor is provided in a form of increased pressure caused by reduction in vein diameter.

In an exemplary embodiment of the invention, the implantation of flow reducing implants in the veins is used to treat diabetic foot syndrome and/or varicose veins. In an exemplary embodiment of the invention, the blood vessels treated include a lower limb vein, for example a superficial vein such as the great or small saphenous veins or their tributaries, or a limb deep vein such as the anterior and posterior tibial or popliteal veins, or a limb perforating vein, such as those in the region of the ankle and the medial side of the lower part of the leg. The degree of reducing and/or size of the flow reducing implant may be the same as used for the coronary sinus and/or be adapted to fit the particular vein being treated.

In an exemplary embodiment of the invention, the implantation procedure is as described above for the coronary sinus, except, of course, that the flow reducing implant is conveyed to a leg vein, rather than to the coronary sinus, for example, via a femoral vein. Desirably, the flow reducing implant is implanted using a trans-vascular approach, for example, from the venous system. In an exemplary embodiment of the invention, the delivery system is inserted through a femoral vein to a deep lower limb vein, such as the popliteal vein or tibial vein. Once in the deep foot vein, the delivery system is guided (e.g., through a sharp bend) to the vein. Alternatively, for example, an open surgery approach may be used instead.

In a particular exemplary embodiment of the invention, a flow reducing implant is placed in a tibial vein and has a narrowing significant enough to encourage the formation of collateral circulation. It is hypothesized that collateral circulation is caused by an increase in venous blood pressure, which, in turn, increases the pressure in the capillaries and/or causes retro-flow in the capillaries and/or causes drainage of the capillaries. Alternative or additional hypotheses that are optionally used to select the constrictive effect of flow reducing implant include:

(a) the flow reducing implant increases the pressure in the foot capillaries, thus increasing perfusion duration;

(b) an increase in resistance of the venous system causes redistribution of blood flow in the ischemic foot; and (c) increasing the arterial diastolic pressure (by restricting venous drainage) activates the sympathetic auto-regulation mechanism.

It should be noted that the selection of flow reducing implant may be made to achieve one or more of the above suggested effects, optionally to a desired degree and/or taking into account safety issues, such as allowing some drainage and maximum pressure allowed by the venous drainage system. These effects may be determined using various measurements, such as a pressure sensor on the implanting catheter.

In an exemplary embodiment of the invention, the selection of the flow reducing implant depends on one or more of:

(a) The lower limb vein length and diameter (e.g., to obtain a matching flow reducing implant geometry);

(b) Desired increase in the lower limb deep venous pressure before flow reducing implant, optionally including a maximum allowed pressure, for example, 50 mm Hg at which a peripheral vein expected to be damaged and/or fail (e.g., to decide what narrowing to select);

(c) Desired narrowing (e.g., to decide what narrowing to select);

(d) Desired later further narrowing (e.g., to decide on flow reducing implant type);

(e) Resistance of the lower limb vein wall (e.g., how elastic or stiff should flow reducing implant be and/or what inflation pressure to use);

(f) Desired redistribution of lower limb blood flow; and/or (g) Desired retro-flow of blood in lower limb arteries and/or veins.

In an exemplary embodiment of the invention, the venous location of the flow reducing implant is selected to match various limb conditions, such as arterial blockage, alternatively or additionally to selecting the reducing diameter for each such flow reducing implant. Alternatively or additionally, the location(s) of implantation are selected to achieve a desired redistribution of lower limb artery pressures and/or blood flow, for example, to increase perfusion of ischemic or hibernating portions of the foot.

In an exemplary embodiment of the invention, the flow reducing implant implantation is combined with an arterial treatment, such as PCTA, stenosis removal (e.g., laser ablation) and/or stenting. The arterial treatment may be applied, for example, before, during or after the venous treatment, possibly during a same use of catheterization facilities. Doppler measurements are optionally used to asses leg perfusion. Alternatively or additionally, other perfusion and/or flow assessment methods may be used. Alternatively or additionally, an angiographic mapping is used before, during or after the procedure, for example to assist in determining what size flow reducing implant to use and/or a test obstruction of the lower limb vein. Such mapping may, for example, assist in determining a desired narrowing dimension of the flow reducing implant that will achieve a desired pressure increase and/or to detect possible side effects in the patient of such a pressure increase.

It is expected that one or more of the following effects is detected (at once and possibly to a greater extent after some delay): retrograde increase in the lower limb venous pressure, with a possible associated retrograde flow and/or improvement of perfusion in some ischemic areas.

It is expected that in some cases after a few weeks, the lower limb perfusion will increase and redistribution of blood flow will improve, even beyond the immediate result of the insertion of the flow reducing implant. Possibly, the autonomic auto-regulation mechanism of the venous flow will be reset and/or restart. After a few months, revascularization is expected, in some cases, to be well established, and significantly improve the clinical picture.

In another example, the flow reducing implant can be adapted to match other ducts or conduits in the body, for example, with respect to size, length, degree of narrowing, degree of elasticity and form of contact with the conduit walls.

In an alternative set of applications a flow reducing implant is used to reduce blood flow to a growth, for example a cancerous growth or other tumors.

A first example in the treatment of tumors is the uterus. The myometrium (inner lining of uterus) gives rise to a common tumor, a leiomyoma, which is a major source of abnormal uterine bleeding and a major indication for hysterectomy. The endometrial cavity is often the site of hyperplasia and neoplasia.

Uterine Leiomyomas, commonly known as fibroids or myomas, are well-circumscribed, benign tumors arising from the smooth muscle of the myometrium. They are composed of smooth muscle and extracellular matrix. Leiomyomas are the most common solid pelvic tumors in women. These are clinically apparent in 20% to 25% of women during the reproductive years, but careful pathologic inspection of the uterus reveals that they are present in more than 80% of women. Leiomyomas are characterized by their location in the uterus. Subserosal leiomyomas are located just under the uterine serosa and may be attached to the corpus by a narrow or a broad base. Intramural leiomyomas are found predominantly within the thick myometrium but may distort the cavity or cause an irregular external uterine contour. Submucous leiomyomas are located just under the uterine mucosa (endometrium). A known treatment is Uterine artery embolization in which small bubbles are freed in a supply vessel (e.g., a Uterine artery), causing embolisms in capillaries of the leiomyoma.

Interestingly, because the uterus receives branches from uterine and ovarian arteries, the uterus has a dual blood supply. The uterine artery is derived from the hypogastric anterior trunk. It crosses over the ureter at the level of the internal os of the cervix and divides into ascending and descending limbs. The ascending limb runs tortuously upward, between the leaves of the broad ligament, and supplies horizontal anterior and posterior branches to the cervix and the corpus. The descending branch of the uterine artery turns inferiorly and supplies the vagina from the lateral aspect. It anastomoses freely with the vaginal artery along its course. The ovarian arterial supply also has branches that anastomose with the ascending limb of the uterine artery.

In accordance with an exemplary embodiment of the invention, a leiomyoma is distinguished from healthy tissue by its degree of collateral vasculature and/or its sensitivity to ischemia.

In an exemplary embodiment of the invention, uterine fibroid tumors are treated by implanting a flow reducing implant in selected uterine arteries, thus causing a reduction of the arterial blood supply of the uterine fibroid tumor, leading to ischemia and gradual necrosis of the tumor.

In an exemplary embodiment of the invention, the procedure is as follows. With the patient under mild intravenous sedation and local anesthesia, a small angiographic catheter is introduced into the femoral artery and guided into the left uterine artery. Arteriography is performed, determining the arteries diameter. A flow reducing implant is then inserted into the artery, causing a narrowing of its diameter. The process is optionally repeated in the right uterine artery. The flow reducing implant reduces arterial blood flow through the uterine arteries and causing ischemic necrosis. Normal myometrium is possibly unharmed because multiple collateral arteries supply it. After the right and left uterine arteries are catheterized, the catheter is removed, and the patient optionally undergoes standard post-arteriographic monitoring and recovery. Optionally, the narrowed section reduces the vessel cross-section by 30%, 50%, 80%, 90% or any other lower, larger or intermediate amount, or even completely occludes the vessel. For example, the narrowed section may have an inner diameter of 0.3 mm, 0.5 mm, 1 mm or any larger, smaller or intermediate size.

As with the coronary application described above, a uterine procedure can be minimally invasive (e.g., using a laparoscope or a catheter), or be applied while performing other surgery.

Another application is treating cancer. In a known treatment of liver cancer, a viscous material is injected into a supply vessel of liver cancer, then a chemical poison is injected and then the vessel is sealed. However, the use of viscous material has various associated dangers, such as causing embolism in the brain and lungs.

In an exemplary embodiment of the invention, a flow reducing implant is used for treating cancer, especially cancer of the liver, for example, isolated liver metastases and for hepatocellular carcinoma and/or other tumors including HCC, colorectal, neuroendocrine, leiomyosarcoma, and melanoma metastases.

In an exemplary embodiment of the invention, malignant tumors are treated by implanting a flow reducing implant in selected arteries that supply the malignant tumors, thus causing a significant reduction of arterial blood to the tumor, leading to tumor-cell hypoxia. This results in a controlled tumor regional ischemia and infarct and subsequent necrosis of tumors in the infarcted region. Optionally, various chemical treatments, such as known in the art are used as well.

The liver is apparently especially amenable to this approach, due to the distinct lobular anatomy of the liver. Another potential factor is the existence of two independent blood supplies to the liver. A further potential factor is the ability of healthy hepatic tissue to compensate for tissue mass lost.

In an exemplary embodiment of the invention, the procedure is as follows. Under local anesthesia and mild sedation, a superselective catheter is inserted via a selected artery and threaded into the desired artery supplying the tumor, for example into the hepatic artery. Angiography is then performed to delineate the organ vasculature and performing various measurements, such as determining the diameter of the artery and measuring the required flow reducing implant diameter, followed by placement of the selected flow reducing implant. An angiographic study allows clear visualization of the hypervascular tumor, which is further studied by means of superselective catheterization. After the flow reducing implant has been placed, and further measurements have optionally been performed, such as pressure studies and another angiographic visualization, the catheter is removed, and the patient undergoes standard post-arteriographic monitoring and recovery.

In an exemplary embodiment of the invention, the method described may be used concurrently with an intraarterial infusion of antineoplastic agents mixed, for example, with iodized oil (Lipiodol (R)), which has been extensively used in the treatment of large HCC tumors, or combined with PEI (Percutaneous ethanol injection). It is expected that alcohol diffusion be easier after the occurrence of the hypoxic/necrotic changes produced by the implant, thus allowing the intranodular injection of larger amounts of ethanol. Moreover, after arterial embolization, the normal washout of the injected ethanol is more difficult in the tumorous area, resulting in potential longer retention of the substance. Various pharmaceuticals may be discharged by the flow reducing implant itself, as known, for example in the art of stents. For example, the flow reducing implant may be coated with various pharmaceuticals or the flow reducing implant may include a dissolving portion or a reservoir.

It will be appreciated that the above described methods of deploying a flow reducing implant may be varied in many ways, including, changing the order of acts, which acts are performed more often and which less often, the type and order of tools used and/or the particular timing sequences used. Further, the location of various elements may be switched, without exceeding the sprit of the disclosure. In addition, a multiplicity of features, both of methods and of implants have been described. It should be appreciated that different features may be combined in different ways. In particular, not all the features shown above in a particular embodiment are necessary in every similar exemplary embodiment of the invention. Further, combinations of features from different embodiments into a single embodiment or a single feature are also considered to be within the scope of some exemplary embodiments of the invention. In addition, some of the features of the invention described herein may be adapted for use with prior art devices, in accordance with other exemplary embodiments of the invention. The particular geometric forms and measurements used to illustrate the invention should not be considered limiting the invention in its broadest aspect to only those forms. Although some limitations are described only as method or apparatus limitations, the scope of the invention also includes apparatus designed to carry out the methods and methods of using the apparatus.

Also within the scope of the invention are surgical kits, for example, kits that include sets of delivery systems and flow reducing implants. Optionally, such kits also include instructions for use. Measurements are provided to serve only as exemplary measurements for particular cases, the exact measurements applied will vary depending on the application. When used in the following claims, the terms "comprises", "comprising", "includes", "including" or the like means "including but not limited to".

It will be appreciated by a person skilled in the art that the present invention is not limited by what has thus far been described. Rather, the scope of the present invention is limited only by the following claims.

The invention claimed is:

1. A method of treating abnormal growth in the body, comprising:
    determining a source blood vessel for the abnormal growth;
    inserting a flow reducing implant into the source blood vessel, said flow reducing implant including a flared section for contacting a blood vessel wall and a narrowed section defining a flow passage; and
    reducing blood flow through the source blood vessel with the flow reducing implant and without completely occluding the source blood vessel, thereby allowing blood flow through the source blood vessel after permanent implantation of the flow reducing implant, and
    wherein the reduced blood flow causes ischemia and necrosis of the abnormal growth.

2. A method according to claim 1, wherein said growth is extant in an organ that is fed from multiple source blood vessels.

3. A method according to claim 1, wherein said growth is fed by a single source blood vessel.

4. A method according to claim 1, wherein said growth comprises a leiomyoma.

5. A method according to claim 1, wherein said growth comprises a malignant tumor.

6. A method according to claim 5, wherein said tumor is a liver tumor.

7. A method according to claim 5, wherein said tumor is an encapsulated tumor.

8. A method according to claim 1, further comprising narrowing the narrowed section after insertion of the flow reducing implant to further reduce blood flow therethrough.

9. A method according to claim 1, wherein said flow reducing implant is defined by a sheet material with slots, a width of said slots varying over said flow reducing implant to control an expanded geometry of said flow reducing implant.

10. A method of using a flow reducing implant for treatment of an abnormal growth in the body comprising:
    determining a source blood vessel for the abnormal growth;
    inserting the flow reducing implant into the source blood vessel, said flow reducing implant including a flared section for contacting a blood vessel wall and a narrowed section defining a flow passage; and
    reducing blood flow through the source blood vessel with the flow reducing implant and without completely occluding the source blood vessel, thereby allowing blood flow through the source blood vessel after permanent implantation of the flow reducing implant, and
    wherein the reduced blood flow causes ischemia and necrosis of the abnormal growth.

11. A method according to claim 10, wherein said flow reducing implant further includes an anchor tab that lies generally in a plane of said flared section, the method further comprising anchoring the flow reducing implant to the source blood vessel with the anchor tab.

* * * * *

UNITED STATES PATENT AND TRADEMARK OFFICE
CERTIFICATE OF CORRECTION

Page 1 of 1

PATENT NO. : 8,556,954 B2
APPLICATION NO. : 12/603518
DATED : October 15, 2013
INVENTOR(S) : Shmuel Ben Muvhar et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 247 days.

Signed and Sealed this
Tenth Day of March, 2015

Michelle K. Lee
*Deputy Director of the United States Patent and Trademark Office*